US005789588A

United States Patent [19]

Takenishi et al.

[11] Patent Number: 5,789,588

[45] Date of Patent: Aug. 4, 1998

[54] CARBODIIMIDE DERIVATIVE

[75] Inventors: Soichiro Takenishi, Tokyo; Osamu Suzuki, Kasubake; Hirohiko Yokomizo, Soka; Tatsuo Ichihara; Gen Masuda, both of Tokyo; Namiko Nakajima, Misato; Kazuko Komiya, Tokyo, all of Japan

[73] Assignee: Nisshinbo Industries, Inc., Tokyo, Japan

[21] Appl. No.: 931,714

[22] Filed: Sep. 16, 1997

Related U.S. Application Data

[62] Division of Ser. No. 577,374, Dec. 22, 1995, Pat. No. 5,700,935.

[30] Foreign Application Priority Data

Dec. 22, 1994 [JP] Japan .................................... 6-335492

[51] Int. Cl.$^6$ .................................................. C07D 495/04

[52] U.S. Cl. .......................... 544/130; 544/131; 544/139; 546/193; 546/199; 546/256; 546/273.1; 548/304.1

[58] Field of Search .................................... 544/130, 139; 548/304.1

[56] References Cited

U.S. PATENT DOCUMENTS 4,895,955 1/1990 Ford et al. .

FOREIGN PATENT DOCUMENTS 1-228500 9/1989 Japan .
6-92968 4/1994 Japan .

OTHER PUBLICATIONS

Langer et al., "Enzymatic Synthesis Of Biotin-Labeled Polynucleotides: Novel Nucleic Acid Affinity Probes", Proc. Natl. Acad. Sci., USA, 78, 6633–6637 (1981).

Rigby, et al., "Labeling Deoxyribonucleic Acid To High Specific Activity in Vitro By Nick Translation With DNA Polymerase I", J. Mol. Biol., 113, 237–251 (1977).

Feinberg et al., "A Technique For Radiolabeling DNA Restriction Endonuclease Fragments To High Specific Activity", Anal. Biochem., 137, 266–267 (1984).

Riley et al., "A Method For Biotinylating Oligonucleotide Probes for Use In Molecular Hybridizations", DNA, 5, 333–337 (1986).

Forster et al., "Non-Radioactive Hybridization Probes Prepared By The Chemical Labelling of DNA And RNA With A Novel Reagent, Photobiotin", Nucl. Acids Res., 13, 745–761 (1985).

Shiga et al., "Synthesis Of A Novel Biotin Derivative That Bears A Diazo Group As The Reactive Site", Anal. Sci., 9, 553–556 (1993).

Reisfeld et al., "Nonradioactive Hybridization Probes Prepared By The Reaction Of Biotin Hydrazide With DNA[1]", Biochem. Biophys. Res. Commun., 142, 519 (1987).

Al-Hakim, et al., "Chemically Synthesized Non-Radioactive Biotinylated Long-Chain Nucleic Acid Hybridization Probes", Biochemical J., 251, 935 (1988).

Bondanszky, et al., "Synthesis Of Biocytin-Containing Peptides", J. Amer. Chem. Soc., 99, 235 (1977).

Jasiewicz, et al., "Selective Retrieval Of Biotin-Labeled Cells Using Immobilized Avidin", Exp. Cell. Res., 100, 213 (1976).

Bayer et al., "The Use Of The Avidin-Biotin Complex As A Total IN Molecular Biology", Methods Biochem. Anal., 26, pp. 1–45, (1980).

Heitzmann, et al., "Use Of The Avidin-Biotin Complex For Specific Staining Of Biological Membranes In Electron Microscopy", Proc. Natl. Acad. Sci., USA 71, 3537 (1974).

Gilham, "An Addition Reaction Specific For Uridine And Guanosine Nucleotides And Its Application To The Modification Of Ribonuclease Action", J. Amer. Chem. Soc., 84, 687 (1962).

*Primary Examiner*—Robert W. Ramsuer
*Attorney, Agent, or Firm*—Wenderoth, Lind & Ponack, L.L.P.

[57] ABSTRACT

The present invention relates to a carbodiimide derivative represented by the following general formula:

$$W_1—X—N=C=N—Y—W_2—Z$$

wherein $W_1$ is a straight chain, branched chain or cyclic saturated or unsaturated aliphatic hydrocarbon group, a substituted or unsubstituted aryl group, a heteroaryl group, a tertiary amino group or a tertiary or quaternary ammonium group; $—W_2—Z$ is a quaternary ammonium group; X and Y are each independently a single bond or an alkylene group; and Z is a biotin group represented by the following formula:

(a)

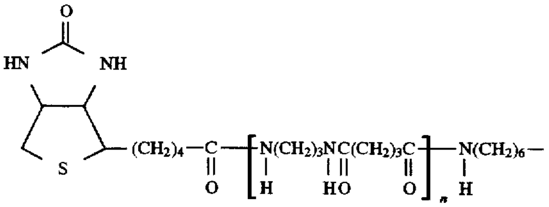

wherein n is 0 or 1.

The derivative is useful as a label reagent for introducing a biotin group into a nucleic acid or a protein.

18 Claims, No Drawings

CARBODIIMIDE DERIVATIVE

This is a divisional application of now allowed Ser. No. 08/577,374 filed Dec. 22, 1995 now U.S. Pat. No. 5,700,935.

The present invention relates to a novel biotin group-containing carbodiimide derivative which is useful as a reagent for introducing a biotin group as a label into a nucleic acid or a protein.

For detection of nucleic acid, labelling of nucleic acid has heretofore been conducted by introducing, into the nucleic acid, a radioisotope (e.g. $^{32}P$, $^{14}C$ or $^{3}H$) as a label compound by a nick translation method, a random primer method, a tailing method or the like. The detection of nucleic acid by using such a radioisotope-labelled nucleic acid, generally has problems in safety, economy, stability, etc. although the method has specificity and a high sensitivity. That is, the radioisotope used must be stored and applied in view of the half-life and allows for neither long-term storage nor repeated use. Further, the radioisotope is generally harmful to human body and must be handled and stored with strict care (a special facility is required for the handling and storage).

Hence, labelling of nucleic acid or protein with a non-radioactive label substance is in wide use. In particular, a method of using biotin (biotin has a high affinity with avidin or streptavidin) is in wide use. As such a method, there is generally used a method which comprises introducing biotin into a nucleic acid, bonding the biotin introduced into the nucleic acid, to an enzyme-labelled avidin, and measuring the activity of the enzyme.

As the method for introducing biotin into a nucleic acid, a method proposed by Langer et al. is well known which comprises bonding biotin to a pyrimidine ring via a linker to form a 2'-deoxyuridine triphosphate derivative [Proc. Natl. Acad. Sci., USA, 78, 6633–6637 (1981)] and introducing the derivative into a nucleic acid by the nick translation method [Rigby et al., J. Mol. Biol., 113, 237–257 (1977)], the random primer method [Feinberg and Vogelstein, Anal. Biochem., 137, 266–267 (1983)], or the tailing method [Riley et al., DNA, 5, 333–337 (1986)].

Also, a method was developed which uses a compound obtained by bonding biotin to a photoactive aromatic azide by the use of a linker arm [Forster et al., Nucl. Acids Res., 13, 745–761 (1985)]. As such a compound, Photobiotin R (a product of BRESA Co.) is commercially available.

Other methods such as the followings are also known. A method using a diazo compound [M. Shiga et al., Anal. Sci., 9, 553–556 (1993)]; a method using biotin hydrazide [Reisfeld et al., Biochem. Biophys. Res. Commun., 142, 519 (1987)]; a method which comprises bonding a biotin derivative having an amino group as a side chain, such as biotin hydrazide derivative, biotin spermine derivative or the like, to a nucleic acid by the use of a bifunctional crosslinking agent such as glutaraldehyde, bisepoxide or the like [Japanese Patent Application Kokai (Laid-Open) No. 228500/1989; AL-Hakim, A. H. et al., Biochemical J., 251, 935 (1988)]; a method using a formyl group-containing biotin derivative [Japanese Patent Application Kokai (Laid-Open) No. 92968/1994]; and so forth.

Introduction of biotin into protein can be conducted by reacting the free amino group of the protein with a p-nitrophenyl ester of biotin [Bondanszky, M. and Fogan, D. T., J. Amer. Chem. Soc., 99, 235 (1977)] or an N-hydroxysuccinimide ester of biotin [Jasiewicz, M. L. et al., Exp. Cell. Res., 100, 213 (1976)]. For conducting the introduction, there are also known a method of using a diazoanilide derivative [Bayer, E. A. et al., Methods Biochem. Anal., 26, (1980)]; a method of using a hydrazide derivative [Heitzmann, H. et al Proc. Natl. Acad. Sci. USA, 71, 3537 (1974)]; and so forth.

The above-mentioned method using an enzyme (e.g. the nick translation method, the random primer method and the tailing method) has various problems. For example, a long time (ordinarily, 1 hour or longer) is required for labelling; strict temperature control (15°–37° C.) is necessary; and no labelling is possible for single-stranded nucleic acids in the nick translation method. Further in the enzyme method, the labelled nucleic acid fragments have a wide molecular weight distribution, often generating nucleic acid fragments of low molecular weight; the labelled nucleic acid synthesized has a restricted length and it is impossible to synthesize a labelled nucleic acid longer than that; the labelling operation has many steps and is complicated. Furthermore in the enzyme method, biotin introduction into a short nucleic acid (e.g. a nucleic acid oligomer) ent impossible; and the enzyme and the biotinylating reagent (i.e. a nucleoside triphosphate-biotin adduct) both used in labelling are very unstable and must be handled and stored carefully.

In the nucleic acid-labelling method using a compound obtained by bonding biotin to a photoactive aromatic azide by the use of a linker arm, the labelling reaction is complete in a relatively short time; however, there are problems in that the reaction must be conducted in a dark place because the above compound containing a photoactive azide group has low stability to light, a special light source must be used in the reaction, thus the reagent handling or storage and the operation employed are complicated. Further in the above method, the efficiency of labelling of relatively short nucleic acid is low, making impossible the biotin introduction into short nucleic acid (e.g. nucleic acid oligomer).

In the nucleic acid-labelling method using a formyl group-containing biotin, the Schiff base formed between aldehyde and amino group is easily hydrolyzed and unstable, and the labelled nucleic acid must be reduced for stabilization. In the nucleic acid-labeling method using a diazo group, since the diazo group-containing biotin is insoluble in water, an organic solvent such as chloroform or the like must be used. In the method of introducing, into a nucleic acid, a biotin hydrazide derivative or the like having an amino group as a side chain, by the use of a bifunctional crosslinking agent, side reactions between biotin hydrazide molecules or between nucleic acid molecules take place easily, which tends to invite reductions in labelling efficiency, specificity of hybridization, etc.

Also in the labelling method of protein (conducted by the methods mentioned above for the labelling of nucleic acid), there are problems basically same as those present in the labelling of nucleic acid.

Hence, it has been strongly desired recently to develop a reagent which allows for the introduction of biotin into nucleic acid or protein, simply and efficiently in a short time without using a special reactor or special reaction conditions.

It is well known that carbodiimide compounds are reactive toward nucleic acids. For example, carbodiimide compounds react with guanine and thymine bases in nucleic acid, having no hydrogen bond, to form adducts [P. T. Gilham, J. Amer. Chem. Soc., 84, 688 (1962)].

The present inventors made an extensive study on the simple and highly efficient introduction of biotin into nucleic acid or protein. As a result, by utilizing the high reactivity of carbodiimide group with nucleic acid, protein, etc. and also by introducing a biotin group into a carbodiimide compound, a reagent has been successfully developed which can introduce biotin into a nucleic acid or a protein and thereby allows for biotin labelling of the nucleic acid or the protein efficiently in a short time.

According to the present invention there is provided a carbodiimide derivative represented by the following general formula (I)

$$W_1—X—N=C=N—Y—W—Z \quad (I)$$

wherein $W_1$ is a straight chain, branched chain or cyclic saturated or unsaturated aliphatic hydrocarbon group, a substituted or unsubstituted aryl group, a heteroaryl group, a tertiary amino group or a tertiary or quaternary ammonium group; $—W_2—Z$ is a quaternary ammonium group; X and Y are each independently a single bond or an alkylene group whose main chain has 1–20 carbon atoms and which may have at least one branch having 24 or less carbon atoms; and Z is a biotin group represented by the following formula (a):

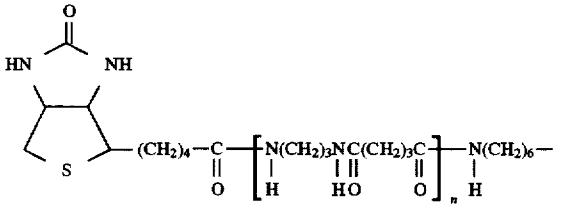
(a)

wherein n is 0 or 1.

In the present specification, the "straight chain, branched chain or cyclic saturated or unsaturated aliphatic hydrocarbon group" includes an alkyl group, an alkenyl group, an alkynyl group and a cycloalkyl group. The alkyl group includes, for example, methyl, ethyl, propyl, isopropyl, butyl, isobutyl, sec-butyl, tert-butyl, pentyl, isopentyl, hexyl, heptyl, octyl, 2-ethylhexyl, nonyl and decyl, with an alkyl group of 1–20 carbon atoms, particularly 1–6 carbon atoms being preferred generally. The alkenyl group includes, for example, vinyl, allyl, crotyl, tiglyl and prenyl, with an alkenyl group of 2–10 carbon atoms, particularly 2–5 carbon atoms being preferred. The alkynyl group can be exemplified by ethynyl and propargyl, with an alkynyl group of 2–10 carbon atoms, particularly 2–5 carbon atoms being preferred generally. The cycloalkyl group includes those having alkyl group(s) on the ring, and can be exemplified by cyclopropyl, cyclopentyl, cyclohexyl, 4-methylcyclohexyl, 4-tert-butylcyclohexyl and cyclooctyl, with a cycloalkyl of 3–14 carbon atoms, particularly 6–10 carbon atoms being preferred generally.

The "aryl group" may be any of monocyclic type or multicyclic type and includes, for example, phenyl and naphthyl. The aryl group may have 1–4, preferably 1–2 substituents which are not substantially reactive with a carbodiimide group. The substituent includes, for example, alkyl groups such as methyl, ethyl, propyl and the like; alkoxy groups such as methoxy, ethoxy and the like; alkylthio groups such as methylthio, ethylthio and the like; alkoxycarbonyl groups such as methoxycarbonyl, ethoxycarbonyl and the like; halogen atoms such as fluorine, chlorine, bromine, iodine and the like; dialkylamino groups such as dimethylamino, diethylamino and the like; cyano group; and nitro group. Examples of the aryl group having such substituent(s) are tolyl, xylyl, methoxyphenyl, methylthiophenyl, methoxycarbonylphenyl, chlorophenyl, bromophenyl, iodophenyl, dimethylaminophenyl, diethylaminophenyl, cyanophenyl and nitrophenyl.

The "aralkyl group" refers to an alkyl group substituted with a substituted or unsubstituted aryl group and includes, for example, benzyl and phenethyl.

The "heteroaryl group" includes monocyclic or polycyclic aromatic heterocyclic group containing at least one, preferably one to three hetero atoms selected from nitrogen, oxygen and sulfur. The heteroaryl group can be exemplified by 5- to 6-membered monocyclic heterocyclic groups such as furyl, thienyl, pyrrolyl, pyridyl and the like; and polycyclic heterocyclic groups such as benzofuryl, xanthenyl, dibenzofuryl, thianthrenyl, indolyl, acridinyl (?) and the like. The cycles of these groups may have the same substituent(s) as mentioned above with respect to the aryl group.

In the general formula (I), $W_1$ is preferably a $C_1$–$C_{20}$, particularly $C_1$–$C_{10}$ alkyl group; or a substituted or unsubstituted aryl group, particularly a phenyl group which may be substituted with at least one, preferably one to two $C_1$–$C_{10}$ alkyl groups (e.g. methyl groups).

In the general formula (I), when $W_1$ is a tertiary amino group or a tertiary or quaternary ammonium group, preferable as these groups are shown below.

(1) A nitrogen-containing heterocyclic group whose nitrogen atom may be quaternized with a hydrogen atom, a straight chain, branched chain or cyclic saturated or unsaturated aliphatic hydrocarbon group, a substituted or unsubstituted aryl or aralkyl group, or a biotin group represented by the formula (a) and whose ring may be substituted with the same substituent(s) as mentioned above with respect to the aryl group. For example, a pyridyl or pyridinium group; particularly a 2-, 3- or 4-pyridyl or pyridinium group whose nitrogen atom may be quaternized with a $C_1$–$C_{10}$ alkyl group (e.g. a methyl group) or a biotin group of the formula (a) and whose ring may be substituted with at least one, preferably one to two $C_1$–$C_{10}$ alkyl groups (e.g. methyl groups). Specific examples are groups represented by the following formulas:

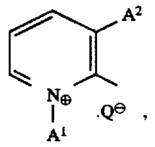

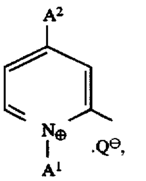

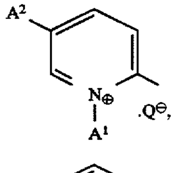

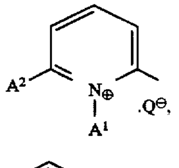

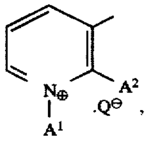

-continued

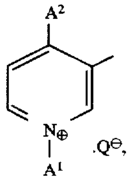

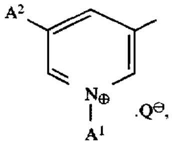

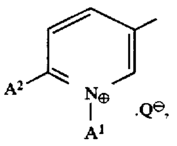

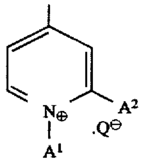

and

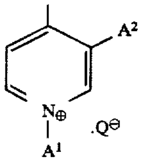

wherein $A^1$ is not present (in this case, neither + of nitrogen atom nor $Q^-$ is present), or is a hydrogen atom, a $C_1$–$C_{10}$ alkyl group, an aryl or aralkyl group which may be substituted with at least one, preferably one to two $C_1$–$C_{10}$alkyl groups, or a biotin group of the formula (a); $A^2$ is a hydrogen atom, a halogen atom, a $C_1$–$C_{10}$ alkyl group, a $C_1$–$C_{10}$ alkoxy group, or an aryl or aralkyl group which may be substituted with at least one, preferably one to two $C_1$–$C_{10}$ alkyl groups, with a hydrogen atom, a chlorine atom, a bromine atom, a methyl group or a methoxy group being preferred; and $Q^-$ is a counter anion such as sulfate ion, alkyl sulfate ion, aryl sulfate ion, halosulfate ion, halide ion or the like.

(2) A tertiary amino group or a tertiary or quaternary ammonium group, represented by the following formula:

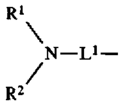

(b)

or

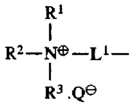

(c)

wherein $R^1$ and $R^2$ are each independently a straight chain, branched chain or cyclic saturated or unsaturated $C_1$–$C_{10}$ aliphatic hydrocarbon group or a substituted or unsubstituted aryl or aralkyl group, particularly a $C_1$–$C_{10}$ alkyl group or a phenyl group which may be substituted with at least one, preferably one to two $C_1$–$C_{10}$ alkyl groups; $R^3$ is a hydrogen atom, a straight chain, branched chain or cyclic saturated or unsaturated $C_1$–$C_{10}$ aliphatic hydrocarbon group, a substituted or unsubstituted aryl or aralkyl group, or a biotin group of the formula (a), particularly a hydrogen atom, a $C_1$–$C_{10}$ alkyl group, a phenyl group which may be substituted with at least one, preferably one to two $C_1$–$C_{10}$ alkyl groups, or a biotin group of the formula (a); $L^1$ is a single bond or an o-, m- or p-phenylene group which may be substituted with at least one, preferably one to two $C_1$–$C_{10}$ alkyl groups; and $Q^-$ is as defined above.

(3) A tertiary amino group or a tertiary or quaternary ammonium group, represented by the following formula:

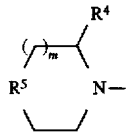

(d)

or

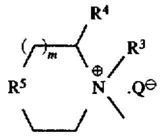

(e)

wherein $R^4$ is a hydrogen atom or $R^1$; $R^1$, $R^3$ and $Q^-$ are as defined above; $R^5$ is an oxygen atom, a sulfur atom or a methylene group; and m is 0 or 1. Specific examples are groups represented by the following formulas:

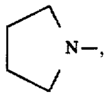

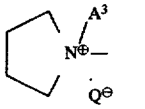

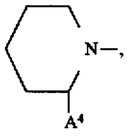

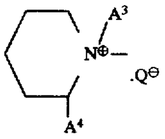

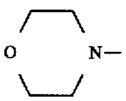

and

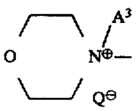

wherein $A^3$ is a hydrogen atom, a $C_1$–$C_{10}$ alkyl group, a phenyl group which may be substituted with at least one, preferably one to two $C_1$–$C_{10}$ alkyl group, or a biotin group of the formula (a); $A^4$ is a hydrogen atom, a $C_1$–$C_{10}$ alkyl group or a phenyl group which may be substituted with at least one, preferably one to two $C_1$–$C_{10}$ alkyl groups, with a hydrogen atom or a methyl group being preferred; and $Q^-$ is as defined above.

(4) A pyrrolidyl, piperidyl, pyrrolidinium or piperidinium group whose 1-position is substituted with a $C_1$–$C_{10}$ alkyl group or a substituted or unsubstituted aryl or aralkyl group, or a 2- or 3-pyrrolidinium or 2-, 3- or 4-piperidinium group whose nitrogen atom is quaternized with a $C_1$–$C_{10}$ alkyl group, a substituted or unsubstituted aryl or aralkyl group, or a biotin group of the formula (a). Specific examples are groups represented by the following formulas:

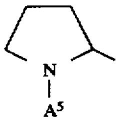,

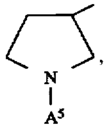,

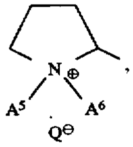,

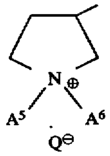

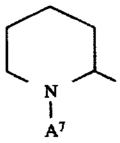,

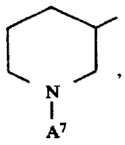,

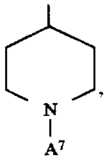,

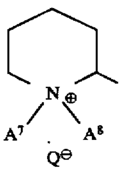,

-continued

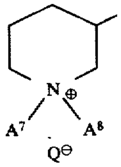

and

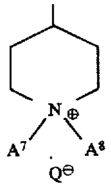

wherein $A^5$ and $A^7$ are each independently a $C_1$–$C_{10}$ alkyl group, or a phenyl or benzyl group which may be substituted with at least one, preferably one to two $C_1$–$C_{10}$ alkyl groups; $A^6$ and $A^8$ are each independently a hydrogen atom, a $C_1$–$C_{10}$ alkyl group, a phenyl or benzyl group which may be substituted with at least one, preferably one to two $C_1$–$C_{10}$ alkyl groups, or a biotin group of the formula (a); and $Q^-$ is as defined above.

In the general formula (I), the quaternary ammonium group represented by —$W_2$—Z can be exemplified by those shown below.

(1) A nitrogen-containing heterocyclic group whose nitrogen atom is quaternized with a biotin group of the formula (a) and whose ring may be substituted with the same substituents as mentioned above with respect to the aryl group; for example, a pyridinium group, particularly a 2-, 3- or 4-pyridinium group whose nitrogen atom is quaternized with a biotin group of the formula (a) and whose ring may be substituted with at least one $C_1$–$C_{10}$ alkyl group or at least one substituted or unsubstituted aryl or aralkyl group, more particularly a 2-, 3- or 4-pyridinium group whose nitrogen atom is quaternized with a biotin group of the formula (a) and whose ring may be substituted with at least one, preferably one to two $C_1$–$C_{10}$ alkyl groups. Specific examples are groups represented by the following formulas:

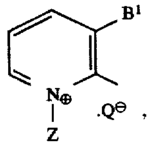,

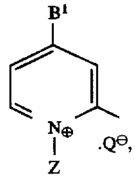,

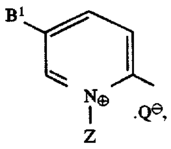,

-continued

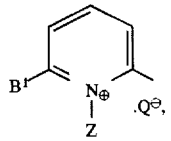

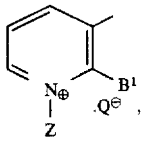

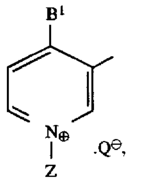

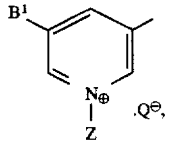

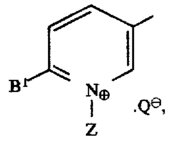

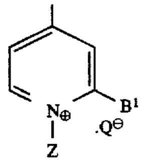

and

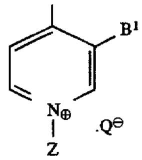

wherein $B^1$ is a hydrogen atom, a halogen atom, a $C_1$–$C_{10}$ alkyl group, a $C_1$–$C_{10}$ alkoxy group, or an aryl or aralkyl group which may be substituted with at least one, preferably one to two $C_1$–$C_{10}$ alkyl groups, with a hydrogen atom, a chlorine atom, a bromine atom, a methyl group or a methoxy group being preferred; and Z and $Q^-$ are as defined above.

(2) A quaternary ammonium group represented by the following formula (f):

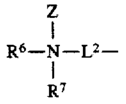

(f)

wherein $R^6$ and $R^7$ are each independently a straight chain, branched chain or cyclic saturated or unsaturated $C_1$–$C_{10}$ aliphatic hydrocarbon group or a substituted or unsubstituted aryl or aralkyl group, particularly a $C_1$–$C_{10}$ alkyl group or a phenyl group which may be substituted with at least one, preferably one to two $C_1$–$C_{10}$ alkyl groups; Z is as defined above; and $L^2$ is a single bond or an o-, m- or p-phenylene group which may be substituted with a $C_1$–$C_{10}$ alkyl group.

(3) A heterocyclic quaternary ammonium group represented by the following formula:

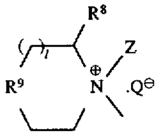

wherein $R^8$ is a hydrogen atom or $R^6$ ; $R^6$ and Z are as defined above; $R^9$ is an oxygen atom, a sulfur atom or a methylene group; and l is 0 or 1. Specific examples are groups represented by the following formulas:

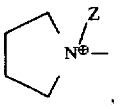

,

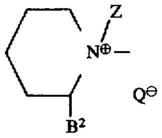

and

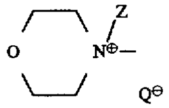

wherein $B^2$ is a hydrogen atom, a $C_1$–$C_{10}$ alkyl group or a phenyl group which may be substituted with at least one, preferably one to two $C_1$–$C_{10}$ alkyl groups, with a hydrogen atom or a methyl group being preferred; and Z is as defined above.

(4) A 2- or 3-pyrrolidinium or 2-, 3- or 4-piperidinium group whose nitrogen atom is quaternized with a biotin group of the formula (a), a $C_1$–$C_{10}$ alkyl group or a substituted or unsubstituted aryl or aralkyl group. Specific examples are groups represented by the following formulas:

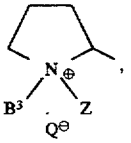

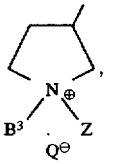

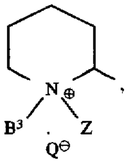

-continued

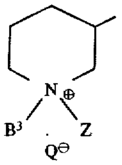

and

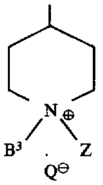

wherein $B^3$ is a $C_1$–$C_{10}$ alkyl group or a phenyl or benzyl group which may be substituted with at least one, preferably one to two $C_1$–$C_{10}$ alkyl groups, with a methyl group, an ethyl group, a phenyl group or a benzyl group being preferred; and Z and $Q^-$ are as defined above.

In the general formula (I), X and Y, which are a linker connecting $W_1$ and the carbodiimide group and a linker connecting the carbodiimide group and —$W_2$—Z, respectively, and which are each independently an alkylene group whose main chain has 1–20 carbon atoms and which may have at least one branch having 24 or less carbon atoms, include the followings, for example.

Methylene, ethylene, trimethylene, propylene, 1-methyltrimethylene, 2-methyltrimethylene, 1,2-dimethyltrimethylene, 2,2-dimethyltrimethylene, tetramethylene, 1-methyltetramethylene, 2-methyltetramethylene, 3-methyltetramethylene, 4-methyltetramethylene, 1,1-dimethyltetramethylene, 1,2-dimethyltetramethylene, 1,3-dimethyltetramethylene, 1,4-dimethyltetramethylene, 2,2-dimethyltetramethylene, 2,3-dimethyltetramethylene, 2,4-dimethyltetramethylene, 3,3-dimethyltetramethylene, 3,4-dimethyltetramethylene, 4,4-dimethyltetramethylene, pentamethylene, 1-methylpentamethylene, 2-methylpentamethylene, 3-methylpentamethylene, 4-methylpentamethylene, 5-methylpentamethylene, 1,1-dimethylpentamethylene, 1,2-dimethylpentamethylene, 1,3-dimethylpentamethylene, 1,4-dimethylpentamethylene, 1,5-dimethylpentamethylene, 2,2-dimethylpentamethylene, 2,3-dimethylpentamethylene, 2,4-dimethylpentamethylene, 2,5-dimethylpentamethylene, 3,3-dimethylpentamethylene, 3,4-dimethylpentamethylene, 3,5-dimethylpentamethylene, 4,4-dimethylpentamethylene, 4,5-dimethylpentamethylene and 5,5-dimethylpentamethylene.

Particularly preferable of these are alkylene groups whose main chain has 1–4 carbon atoms and which may have a methyl group as a branch, such as methylene, ethylene, trimethylene, 1-methyltrimethylene, 1-methyltetramethylene, 2,2-dimethyltrimethylene and the like.

The synthesis of the present carbodiimide derivative as a biotin-introducing reagent can be achieved generally by converting a primary amine as starting material to a urea or thiourea derivative and subjecting the derivative to dehydration or oxidative sulfur elimination. When a symmetrical carbodiimide derivative is synthesized, there can also be used a reaction for subjecting an isocyanate compound to condensation associated with decarbonylation.

For example, a primary amine (II) is condensed with urea to obtain a mono-substituted urea (III); the mono-substituted urea (III) is reacted with a second primary amine or the same primary amine (IV) to obtain a di-substituted urea intermediate (V). That is, a primary amine (II) or a salt thereof and urea are heated in water or other appropriate solvent to give rise to a reaction for several hours; to the reaction mixture or to the separated mono-substituted urea (III) is added a second primary amine or the same primary amine (IV), and a reaction is conducted under the same conditions; thereby, a di-substituted urea intermediate (V) can be synthesized [T. L. Davis and K. C. Blanchard, Org. Synth. Coll., Vol. 1, 453, (1941)].

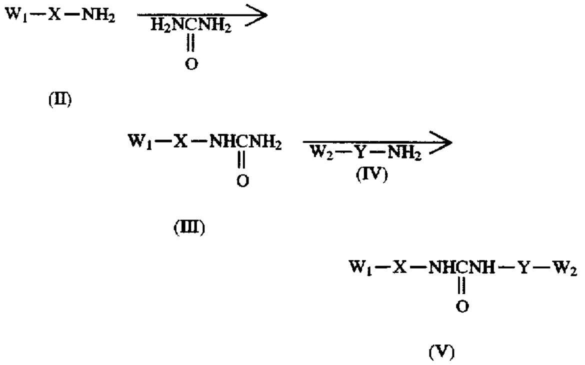

The mono-substituted urea (III) can be synthesized also by reacting a primary amine (II) with cyanic acid or a salt thereof [F. Kurzer, Org. Synth. Coll., Vol. 4, 49 (1963)].

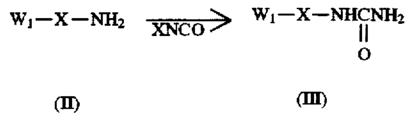

The thus-obtained mono-substituted urea derivative (III) can be converted to a di-substituted urea derivative (V) by the above-mentioned method. When a di-substituted urea derivative (V) is obtained directly, a reaction between an isocyanate compound (VI) and a primary amine (IV) can be used [J. H. Saunders and R. Slocombe, Chem. Rev., 43, 203 (1948)].

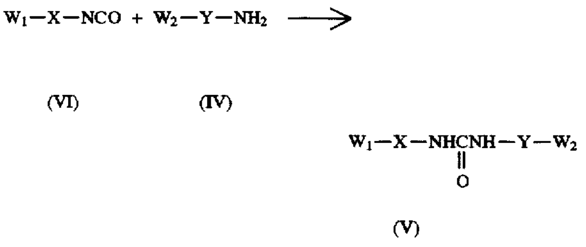

Meanwhile, a di-substituted thiourea derivative (VIII) is generally synthesized by reacting a primary amine (IV) with an isothiocyanate (VII) [N. A. Ivanov, R. V. Viasova, V. A. Gancharava and L. N. Smirnov, Izv. Vyssh. Uchebn. Zaved. Khim. Khim. Tekhnol., 19 (7), 1010 (1976)].

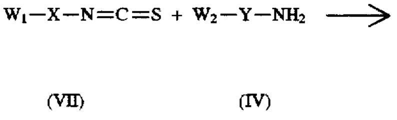

-continued

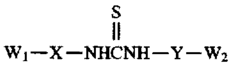

(VIII)

The di-substituted thiourea derivative (VIII) can be synthesized also by reacting a primary amine (II) with carbon disulfide |W. W. Levis, Jr. and E. A. Waipert, U.S. Pat. No. 3,168,560 (1965)|.

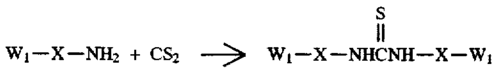

(II) (VIII)

The thus-synthesized di-substituted urea derivative (V) or di-substituted thiourea derivative (VIII) can be converted to a carbodiimide derivative (IX) by dehydration or oxidative sulfur elimination.

The synthesis of the carbodiimide derivative (IX) by dehydration of the di-substituted urea derivative (V) can be easily achieved by heating the urea derivative (V) with p-toluenesulfonic acid chloride in a tertiary amine [G. Amiard and R. Heymes, Bull. Soc. Chim. Fr., 1360 (1956)].

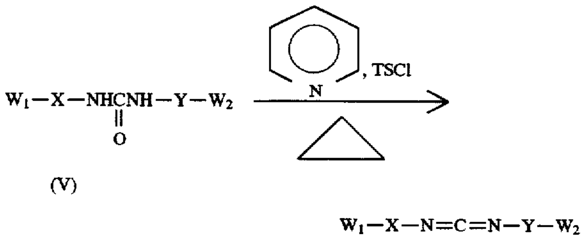

(V)

(IX)

The dehydration of the di-substituted urea derivative (V) can be conducted also by reacting the urea derivative (V) with p-toluenesulfonic acid chloride and potassium carbonate in the presence of a quaternary ammonium salt [Zsuzsa M. Jaszay et al., Synthesis, 520 (1987)].

The sulfur elimination from the di-substituted thiourea derivative (VIII) is conducted generally by using mercury oxide as a sulfur-eliminating agent. The solvent preferably used in this reaction includes, for example, ether, benzene and acetone.

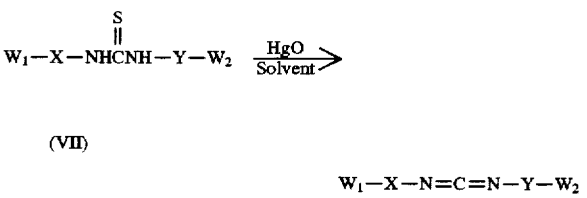

(VII)

(IX)

As the sulfur-eliminating agent other than mercury oxide, there can be used lead oxide |F. Zetzehe and A. Fredrich, Chem. Ber., 73, 1114 (1940)|, zinc oxide |R. F. Coles, U.S. Pat. No. 2,946,819 (1960)|, lead carbonate, lead nitrate and lead chloride |J. C. Sheehan, U.S. Pat. No. 3,135,748 (1964)|, etc. The thiourea derivative (VIII) can also be reacted with sodium hypochlorite in an alkaline solution to obtain a carbodiimide derivative (IX) |H. Stetter and C. Wulff, Chem. Ber., 95, 2302 (1962)|. For example, the thiourea derivative (VIII) is reacted with sodium hypochlorite, sodium carbonate and copper chloride in a solvent such as methylene chloride or the like at a temperature of 0° C. or less for 24 hours; thereafter, separation and purification is conducted by an ordinary method to obtain a carbodiimide derivative (IX).

The thus-obtained carbodiimide derivative (IX) is reacted with a halogenated biotin, preferably brominated or iodinated biotin, whereby a carbodiimide derivative of formula (I) according to the present invention can be obtained.

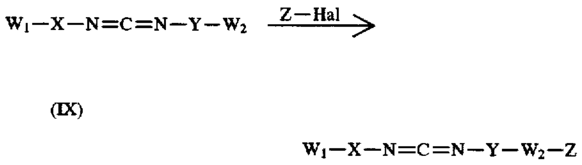

(IX)

(I)

The carbodiimide derivative of the present invention is useful as a biotin-introducing reagent used for biotin labelling of nucleic acid or protein.

For example, biotin labelling of a nucleic acid by introducing a biotin group into the nucleic acid using the carbodiimide derivative of the present invention can be conducted very simply and in a short time, merely by mixing the carbodiimide derivative of the present invention and the nucleic acid in an appropriate buffer solution (e.g. a borate buffer solution) and reacting them at room temperature to about 100° C., preferably at room temperature to about 90° C. for about 1–10 minutes.

The introduction of biotin group using the present carbodiimide derivative can be made to any nucleic acids of various lengths and shapes (e.g. single-stranded and double-stranded) which can be procured generally. For example, while biotin introduction to relatively short-chain nucleic acid (e.g. nucleic acid oligomer) is impossible in the enzyme method or the method using a photoactive azide group-containing compound, both mentioned above, biotin introduction can be efficiently conducted even to such a relatively short-chain nucleic acid with the carbodiimide derivative of the present invention. Further, while in the enzyme method, the labelling reaction tends to invite reduction in molecular weight and consequently biotin introduction to long-chain nucleic acid is impossible, either, efficient biotin introduction even to long-chain nucleic acid (e.g. M13 type or λ type nucleic acid) without reduction in molecular weight is possible with the carbodiimide derivative of the present invention. Furthermore, the efficient biotin introduction to short-chain or long-chain nucleic acid with the present carbodiimide derivative is possible even when the nucleic acid is single-stranded or double-stranded. Moreover, the carbodiimide derivative of the present invention is stable even in an aqueous solution in a dark place. For example, when an aqueous solution of the present compound is allowed to stand in a laboratory room for about a month, there is no change in the properties of the compound; thus, the present compound requires no special control in handling and storage.

Proteins can be subjected to the same biotin labelling as above, with the carbodiimide derivative of the present invention.

The nucleic acid or protein biotin-labelled as above can be purified by various methods such as ethanol precipitation, fractionation with Sephadex G-50 (a carrier for gel filtration chromatography, a product of Pharmacia Co.), electrophoresis and the like; or can be used for hybridization as it is. The biotin-labelled nucleic acid or protein before or after purification can be stored for a long period of time.

The biotin-labelled nucleic acid or protein can be used for detection of nucleic acids or proteins generally as follows. The nucleic acids or proteins, which can be detected, include those of animal, plant and microorganism origin.

First in the case of nucleic acid detection, a nucleic acid immobilized on a solid phase (e.g. a membrane for blotting, a microtiter plate or beads) by covalent bonding, physical adsorption or the like is contacted with a biotin-labelled probe; they are subjected to hybridization; thereafter, unreacted biotin-labelled probe is removed by washing. The solid phase carrier used for immobilization of nucleic acid includes, for example, a nylon membrane, a nitrocellulose membrane, a denatured cellulose membrane and a polyvinylidene difluoride (PVDF) membrane. As the method for immobilizing a nucleic acid to be detected, on a solid phase, there can be used a per se known method such as Southern blotting, dot blotting, colony plaque blotting or the like [Maniatis, M., Molecular Cloning, 1989]. The hybridization between nucleic acid immobilized on solid phase and biotin-labelled nucleic acid can be conducted using such a solution and such a temperature as considered to be most appropriate in view of, for example, (1) the length of the base portions subjected to hybridization and (2) the sequence of the nucleic acid. In order to suppress non-specific adsorption, a Denhardt's solution, skim milk, sodium salt of lauryl sulfate or the like may be added as necessary.

Next, the hybridization product is contacted with an avidin or streptavidin labelled with an enzyme, a fluorescent substance or the like, to allow the biotin of the probe (bonded to the nucleic acid immobilized on the solid phase carrier) to form a biotin-avidin composite or a biotin-streptavidin composite. The composite is subjected to measurement of enzymatic activity, fluorescent intensity or the like and detected. When the measurement of enzymatic activity is conducted, there is used a composite between avidin or streptavidin and an enzyme (e.g. alkaline phosphatase, peroxidase, β-galactosidase or glucose oxidase); thereto is added a substrate which develops a color or emits a light by an enzymatic reaction; and the degree of color development, the intensity of light emission or the like obtained is measured to determine the enzymatic activity.

Meanwhile, the biotin-labelled protein can be subjected also to enzyme immunoassay (EIA). In this case, a target substance is captured on a solid phase carrier (e.g. membrane, microtiter plate or beads) to which an antibody has been bonded; a biotin-labelled antibody is captured to bond the biotin to the target substance. Thereafter, the same detection as for nucleic acid can be used.

By these detections, nucleic acids and proteins can be detected at a high sensitivity because (1) the coupling constant of biotin-avidin composite is very high ($10^{-15}$ $mole^{-1}$) (Green, N. M., Adv. Protein Chem., Vol. 29, p.85, 1975) and (2) avidin has four bonding sites to biotin.

As stated above, use of the carbodiimide derivative of the present invention allows for highly efficient introduction of biotin group into nucleic acid or protein without requiring any special reactor or reaction conditions; and use of a thus-obtained biotin-labelled nucleic acid or protein allows for detection of nucleic acids or proteins of organism origin at a high sensitivity.

The present invention is hereinafter described more specifically by way of Examples.

SYNTHESIS OF COMPOUNDS

SYNTHESIS EXAMPLE 1

Synthesis of Symmetrical Urea (Compound 36–2 Precursor)

There were mixed 32 g (0.25 mole) of 3-(1-pyrrolidyl) propylamine, 6 g (0.1 mole) of urea and 50 ml of xylene. The mixture was refluxed for 24 hours and allowed to cool. The resulting crystals were collected by filtration, washed with benzene and purified by silica gel column chromatography (chloroform/methanol) to obtain 28 g (yield: 79%) of a urea derivative.

SYNTHESIS EXAMPLE 2

Synthesis 1 of Unsymmetrical Urea (Compound 19-2 Precursor)

In 300 ml of water were dissolved 35.9 g (0.25 mole) of p-toluidine hydrochloride, 40.1 g (0.50 mole) of potassium isocyanide and 14.0 g (0.25 mole) of potassium hydroxide. The solution was refluxed with stirring for 2 hours and cooled. The reaction mixture was extracted with chloroform. The extract was dried over potassium carbonate and purified by silica gel column chromatography (chloroform/methanol=9/1) to obtain 22 g (yield: 59%) of an urea derivative.

Fifteen gram (0.1 mole) of the urea derivative was refluxed for 24 hours together with 12 g (0.1 mole) of 3-aminomethyl-4-methylpyridine and 200 ml of xylene, followed by cooling. The resulting crystals were collected by filtration and purified by silica gel column chromatography to obtain 13 g (yield: 51%) of a disubstituted urea derivative.

SYNTHESIS EXAMPLE 3

Synthesis 2 of Unsymmetrical Urea (Compound 15-2 Precursor)

Cyclohexyl isocyanate (1 ml, 7.8 m mol) was dropwise added slowly to 20 ml of a methylene chloride solution containing 1.07 g (7.8 m mol) of N,N-dimethylphenylenediamine, which was being stirred and ice-cooled. After the completion of the dropwise addition, the mixture was stirred at room temperature overnight. The reaction mixture was mixed with water, followed by extraction with methylene chloride. The extract was dried over potassium carbonate and then concentrated. The concentrate was washed with ether to obtain 1.97 g (yield: 96%) of a urea derivative.

SYNTHESIS EXAMPLE 4

Synthesis of Symmetrical Thiourea (Compound 30–1 Precursor)

N,N-dimethylethylenediamine was (8.8 g, 0.1 mole) dissolved in 7 ml of ethanol and the solution was ice-cooled. Thereto was added 3.8 g (0.05 mole) of carbon disulfide during 5 minutes. The mixture was stirred for 1 hour in that state and then refluxed for 5 hours. The reaction mixture was subjected to distillation to remove ethanol, and the residue was purified by silica gel column chromatography (chloroform/methanol=9/1) to obtain 8.7 g (yield: 80%) of a symmetrical thiourea.

SYNTHESIS EXAMPLE 5

Synthesis of Unsymmetrical Thiourea (Compound 19–1 Precursor)

Phenyl isothiocyanate (1.35 g, 10 m mol) was dissolved in 7 ml of anhydrous methylene chloride, and the solution was cooled in an ice bath. Thereto was added 1.2 g (10 m mol) of 2-(2-aminoethyl)pyridine dissolved in 3 ml of anhydrous methylene chloride. The mixture was stirred at room temperature for 15 minutes. The reaction mixture was mixed with water, followed by extraction with methylene chloride. The extract was dried with anhydrous potassium carbonate and concentrated to obtain 2.8 g of a crude product. It was purified by silica gel column chromatography (chloroform:methanol=9/1) to obtain 2.3 9 (yield: 88%) of N-phenyl-N'-2-pyridyl ethyl urea.

SYNTHESIS EXAMPLE 6

Synthesis 1 of Carbodiimide (Compound 19-2Precursor) from Urea

There were mixed 12 g (47 m mol) of N-p-tolyl-N'-(4-methyl-3-pyridyl)methylurea, 35 ml of methylene chloride and 18 ml of triethylamine. The mixture was stirred. Thereto was dropwise added a methylene chloride solution containing 10.5 g (59 m mol) of p-toluenesulfonic acid chloride, at a temperature of 10° C. or less. The mixture was stirred for 30 minutes, then refluxed for 3 hours, and cooled. The insolubles were removed by filtration and the filtrate was subjected to distillation to remove the solvent to obtain crystals. The crystals were washed with ether three times to obtain 6.9 g (yield: 62%) of a carbodiimide.

SYNTHESIS EXAMPLE 7

Synthesis 2 of Carbodiimide (Compound 15-2 Precursor) from Urea

Potassium carbonate (3.53 g, 40 m mol) and 0.23 g (1 m mol) of benzyltriethylammonium chloride were added to 70 ml of a benzene/chloroform (2/1) solution containing 2.61 g (10 m mol) of N-cyclohexyl-N'-(4-dimethylaminophenyl) urea and 1.91 g (10 m mol) of p-toluenesulfonic acid chloride. The mixture was subjected to a reaction for 3 hours under refluxing. The insolubles were removed by filtration. The filtrate was washed with 10 ml of water twice, dried over magnesium sulfate, and subjected to distillation to remove the solvent to obtain 2.02 g (yield: 83%) of a carbodiimide.

SYNTHESIS EXAMPLE 8

Synthesis of Carbodiimide (Compound 19-1 Precursor) from Thiourea

N-phenyl-N'-pyridylethylthiourea (3.8 g, 15 m mol) was dissolved in 50 ml of acetone. Thereto was added 6 g (28 m mol) of mercury oxide. The mixture was refluxed for 6 hours. The reaction mixture was filtered and the filtrate was subjected to distillation to remove the solvent. Ether was added to the residue. The resulting precipitate was collected by filtration and purified by silica gel thin-layer chromatography to obtain 2.0 g (yield: 60%) of N-phenyl-N-2-pyridylethylcarbodiimide.

SYNTHESIS EXAMPLE 9

Introduction of Quaternary Salt (Compound 15-2)

N-cyclohexyl-N'-(4-dimethylaminophenyl)carbodiimide (0.21 g, 0.81 m mol) was dissolved in 9 ml of anhydrous dimethylformamide. Thereto was added 0.37 g (0.81 m mol) of N-(6-iodohexyl)biotinamide. The mixture was stirred at room temperature for 24 hours and then subjected to distillation under reduced pressure to remove dimethylformamide. The resulting white powder was washed with ether and then dissolved in methanol. Thereto was added ether to give rise to reprecipitation to obtain 0.15 g (yield: 77%) of compound 15-2.

SYNTHESIS EXAMPLE 10

Introduction of Two Different Quaternary Salts (Compound 29-1)

N-(2-pyridylmethyl)-N'-(2-diethylaminoethyl) carbodiimide (0.21 g, 0.91 m mol) was dissolved in 10 ml of benzene. Thereto was added 0.13 g (0.92 m mol) of methyl iodide. The mixture was stirred for 24 hours. The resulting precipitate was collected by filtration and washed with benzene to obtain 0.31 g (yield: 92%) of an ammonium salt. This ammonium salt (0.31 g, 0.83 m mol) was dissolved in 10 ml of anhydrous dimethylformamide. Thereto was added 0.38 g (0.84 m mol) of N-(6-iodohexyl)biotinamide, and the mixture was stirred for 20 hours. The reaction mixture was subjected to distillation to remove dimethylformamide. Water was added to the residue. The resulting insolubles were removed by filtration. The filtrate was freeze-dried to obtain 0.48 g (yield: 70%) of compound 29-1.

SYNTHESIS EXAMPLE 11

Introduction of Two Same Quaternary Salts (Compound 27-2)

N-3-pyridyl-N'-2-(N-methylpyrrolidyl)ethylcarbodiimide (0.22 g, 0.96 m mol) was dissolved in 10 ml of benzene. Thereto was added 0.44 g (0.97 m mol) of N-(6-iodohexyl) biotinamide. The mixture was stirred for 24 hours. The resulting precipitate was collected by filtration and washed with benzene to obtain a pyridinium salt. This salt (0.34 g, 0.50 m mol) was dissolved in 10 ml of dimethylformamide. Thereto was added 0.31 g (0.50 m mol) of $Z_1$—I. The mixture was stirred for 26 hours and then subjected to distillation under reduced pressure to remove dimethylformamide. Water was added to the residue. The resulting insolubles were removed by filtration. The filtrate was freeze-dried to obtain 0.48 g (yield: 73%) of compound 27-2.

SYNTHESIS EXAMPLE 12

Synthesis of $Z_0$—I

Biotin (2.0 g, 8.2 m mol) was dissolved in 160 ml of anhydrous dimethylformamide. Thereto was added 2.6 ml of tributylamine. The mixture was stirred for 10 minutes. Thereto was added 1.2 ml of isobutyl chloroformate. The mixture was stirred for 30 minutes. The reaction mixture was added, at a temperature of −5° C. or less in 30 minutes, to a solution of 1.1 g (9.6 m mol) of 6-amino-1-hexanol dissolved in 160 ml of anhydrous dimethylformamide, cooled to −5° C . The mixture was stirred at 0° C. for 3 hours. The reaction mixture was subjected to distillation under reduced pressure to remove dimethylformamide to obtain a crude product. This crude product was purified by silica gel column chromatography (chloroform/methanol) to obtain 2.2 g (yield: 78%) of a hydroxyl derivative. This N-(6-hydroxyhexyl)biotinamide (2.2 g, 6.4 m mol) was dissolved in 65 ml of anhydrous dimethylformamide. Thereto was added 5.2 g (13 m mol) of methyltriphenoxyphosphonium iodide. The mixture was stirred at room temperature for 1 hour under light shielding. Methanol (1.7 ml) was added, followed by stirring for 20 minutes. The reaction mixture was subjected to distillation under reduced pressure to remove the solvent. The residue was purified by silica gel column chromatography (chloroform/methanol) to obtain 2.2 g (yield: 76%) of a biotin iodide.

SYNTHESIS EXAMPLE 13

Synthesis of $Z_0$—Br

N-(6-hydroxyhexyl)biotinamide (2.2 g, 6.4 m mol) was dissolved in 70 ml of methylene chloride. Thereto were added, in a nitrogen atmosphere at room temperature, 2.0 g (7.6 m mol) of triphenylphosphine and 3.2 g (9.6 m mol) of carbon tetrabromide. The mixture was stirred for 1 hour. The reaction mixture was washed with a saturated aqueous sodium bicarbonate solution. The organic layer was washed with a saturated aqueous sodium chloride solution, dried over anhydrous magnesium sulfate, and concentrated. The concentrate was purified by silica gel column chloromatography (chloroform/methanol) to obtain 2.0 g (yield: 77%) of a biotin bromide.

SYNTHESIS EXAMPLE 14

Synthesis of $Z_0$—Cl

N-(6-hydroxyhexyl)biotinamide was (2.2 g, 6.4 m mol) mixed with 70 ml of anhydrous carbon tetrachloride. Thereto was added 2.0 g (7.6 m mol) of triphenylphosphine in a nitrogen atmosphere at room temperature. The mixture was refluxed with heating. One hour later, the reaction mixture was washed with a saturated aqueous sodium bicarbonate solution, dried over anhydrous magnesium sulfate, and concentrated. The concentrate was purified by silica gel column chromatography to obtain 1.4 g (yield: 60%) of a biotin chloride.

SYNTHESIS EXAMPLE 15

Synthesis of $Z_1$—I

Biotin (2.0 g, 8.2 m mol) was dissolved in 160 ml of anhydrous dimethylformamide. Thereto was added 2.6 ml of tributylamine. The mixture was stirred for 10 minutes. Thereto was added 1.2 ml of isobutyl chloroformate. The mixture was stirred for 30 minutes. The reaction mixture was added, at a temperature of −5° C. or less in 30 minutes, to a solution of 2.8 g (9.8 m mol) of 8,12-dioxo-7,13-diaza-16-amino-1-hexadecanol dissolved in 160 ml of anhydrous dimethylformamide. The mixture was stirred at 0° C. for 3 hours. The reaction mixture was subjected to distillation under reduced pressure to remove dimethylformamide to obtain a crude product. This crude product was purified by silica gel column chloromatography (chloroform/methanol) to obtain 3.1 g (yield: 74%) of a hydroxyl derivative. This N-(5,9-dioxo-4,10-diaza-16-hexadecanol )biotinamide (3.3 g, 6.4 m mol) was dissolved in 65 ml of anhydrous dimethylformamide. Thereto was added 5.2 g (13 m mol) of methyltriphenoxyphosphonium iodide. The mixture was stirred at room temperature for 1 hour under light shielding. Methanol (1.7 ml) was added, followed by stirring for 20 minutes. The reaction mixture was subjected to distillation under reduced pressure to remove the solvent. The residue was purified by silica gel column chloromatography (chloroform/methanol) to obtain 3.0 g (yield: 76%) of a biotin iodide.

SYNTHESIS EXAMPLE 16

Quaternization with Methyl Tosylate (Compound 30-8 Precursor)

Bis(3-dimethylaminopropyl)carbodiimide (3.61 g, 17 m mol) was dissolved in 35 ml of anhydrous diethyl ether. The solution was cooled to a temperature of 10° C. or less. Thereto was added 2.23 g (12 m mol) of methyl p-toluenesulfonate. The mixture was stirred for 24 hours. The resulting crystals were collected by filtration and washed with ether three times to obtain 4.21 g (yield: 88%) of a compound 30–8 precursor.

In accordance with the procedures described in the above Synthesis Examples, compounds of the present invention were synthesized. Their serial numbers are shown in Table 1 together with the Synthesis Example Nos. used and yields obtained in the steps of (thio)urea synthesis, carbodiimide synthesis and quaternary salt synthesis for production of each present compound.

TABLE 1

| Compound No. | Synthesis of urea (Synthesis Example No. and yield) | Synthesis of thiourea (Synthesis Example No. and yield) | Synthesis of carbodiimide (Synthesis Example No. and yield) | Synthesis of quaternary salt (Synthesis Example No. and yield) |
|---|---|---|---|---|
| 14-1 | | 5 ,95% | 8 ,80% | 9 ,90% |
| 14-2 | 3 ,90% | | 7 ,65% | 9 ,90% |
| 14-3 | 3 ,92% | | 7 ,72% | 9 ,91% |
| 14-4 | | 5 ,92% | 8 ,80% | 9 ,90% |
| 15-1 | | 5 ,86% | 8 ,85% | 9 ,92% |
| 15-2 | 3 ,96% | | 7 ,83% | 9 ,77% |
| 15-3 | 3 ,91% | | 7 ,65% | 9 ,88% |
| 16-1 | | 5 ,90% | 8 ,68% | 9 ,88% |
| 16-2 | 3 ,96% | | 7 ,72% | 9 ,60% |
| 17-1 | | 5 ,97% | 8 ,78% | 9 ,62% |
| 17-2 | 3 ,89% | | 7 ,90% | 9 ,69% |
| 18-1 | | 5 ,91% | 8 ,92% | 9 ,68% |
| 18-2 | 3 ,87% | | 7 ,83% | 9 ,79% |
| 18-3 | 3 ,91% | | 7 ,79% | 9 ,52% |
| 18-4 | 3 ,89% | | 7 ,81% | 9 ,59% |
| 19-1 | | 5 ,88% | 8 ,60% | 9 ,90% |
| 19-2 | 3 ,88% | | 6 ,55% | 9 ,85% |
| 19-3 | 3 ,82% | | 6 ,58% | 9 ,78% |
| 19-4 | | 5 ,85% | 6 ,46% | 9 ,90% |
| 20-1 | | 5 ,92% | 8 ,75% | 9 ,96% |
| 20-2 | 3 ,80% | | 7 ,80% | 9 ,94% |
| 20-3 | 3 ,86% | | 7 ,82% | 9 ,90% |
| 20-4 | | 5 ,86% | 8 ,85% | 9 ,88% |
| 21-1 | 3 ,96% | | 7 ,76% | 9 ,67% |
| 21-2 | 3 ,37&63% | | 6 ,62% | 9 ,55% |
| 21-3 | 3 ,91% | | 7 ,75% | 9 ,59% |
| 21-4 | | 5 ,82% | 8 ,68% | 9 ,48% |
| 22-1 | 3 ,83% | | 7 ,73% | 9 ,59% |
| 22-2 | 2 ,42&60% | | 6 ,60% | 9 ,61% |
| 22-3 | 3 ,78% | | 6 ,48% | 9 ,69% |
| 22-4 | | 5 ,90% | 8 ,69% | 9 ,70% |
| 23-1 | 2 ,42&50% | | 6 ,51% | 9 ,70% |
| 23-2 | 3 ,83% | | 6 ,48% | 9 ,64% |
| 24-1 | 2 ,37&57% | | 6 ,47% | 11 ,86% |
| 24-2 | 2 ,60&57% | | 6 ,38% | 11 ,80% |
| 24-3 | 2 ,38&62% | | 6 ,42% | 10 ,89&82% |
| 24-4 | | | 8 ,78% | 11 ,90% |
| 25-1 | | 5 ,89% | 8 ,90% | 9 ,93% |
| 25-2 | 2 ,60&50% | | 6 ,49% | 9 ,91% |

TABLE 1-continued

| Compound No. | Synthesis of urea (Synthesis Example No. and yield) | Synthesis of thiourea (Synthesis Example No. and yield) | Synthesis of carbodiimide (Synthesis Example No. and yield) | Synthesis of quaternary salt (Synthesis Example No. and yield) |
|---|---|---|---|---|
| 25-3 | 2 ,42&52% | | 6 ,61% | 10 ,96&78% |
| 25-4 | 2 ,65&38% | | 6 ,57% | 10 ,75&80% |
| 25-5 | 2 ,53&54% | | 6 ,60% | 11 ,79% |
| 25-6 | 2 ,68&46% | | 6 ,46% | 11 ,75% |
| 25-7 | | 5 ,86% | 8 ,75% | 9 ,90% |
| 26-1 | 2 ,72&39% | | 6 ,46% | 9 ,70% |
| 26-2 | 2 ,70&45% | | 6 ,63% | 9 ,68% |
| 26-3 | | 5 ,86% | 8 ,79% | 11 ,72% |
| 26-4 | 2 ,35&70% | | 6 ,39% | 11 ,72% |
| 26-5 | 2 ,62&48% | | 6 ,52% | 10 ,70&65% |
| 27-1 | 2 ,63&67% | | 6 ,59% | 9 ,65% |
| 27-2 | 2 ,63&58% | | 6 ,58% | 10 ,90&63% |
| 27-3 | 2 ,56&48% | | 6 ,53% | 11 ,83% |
| 28-1 | 2 ,61&48% | | 6 ,52% | 9 ,72% |
| 28-2 | 2 ,42&48% | | 6 ,61% | 10 ,91&72% |
| 28-3 | 2 ,46&53% | | 6 ,50% | 11 ,78% |
| 29-1 | 2 ,51&52% | | 6 ,62% | 10 ,92&70% |
| 29-2 | 2 ,55&52% | | 6 ,68% | 10 ,82&83% |
| 29-3 | 2 ,36&38% | | 6 ,42% | 11 ,93% |
| 29-4 | 2 ,39&60% | | 6 ,58% | 10 ,90&88% |
| 30-1 | | 4 ,80% | 8 ,88% | 11 ,95% |
| 30-2 | | 5 ,93% | 8 ,88% | 10 ,90&89% |
| 30-3 | 2 ,64&73% | | 6 ,60% | 11 ,92% |
| 30-4 | 2 ,47&65% | | 6 ,60% | 10 ,99&78% |
| 30-5 | 1 ,90% | | 6 ,82% | 10 ,93&90% |
| 30-6 | 1 ,90% | | 6 ,82% | 10 ,93&88% |
| 30-7 | 1 ,90% | | 6 ,82% | 11 ,91% |
| 30-8 | 1 ,90% | | 6 ,82% | 16 ,90%<br>9 ,87% |
| 31-1 | 2 ,62&4 8% | | 6 ,49% | 11 ,76% |
| 31-2 | | 5 ,92% | 8 ,80% | 11 ,68% |
| 31-3 | 2 ,72&63% | | 6 ,58% | 11 ,75% |
| 31-4 | | 5 ,92% | 8 ,75% | 11 ,68% |
| 31-5 | | 5 ,91% | 8 ,87% | 16 ,87%<br>9 ,90% |
| 32-1 | 2 ,68&53% | | 6 ,43% | 11 ,76% |
| 32-2 | 2 ,65&48% | | 6 ,49% | 11 ,74% |
| 32-3 | 2 ,39&51% | | 6 ,49% | 11 ,65% |
| 32-4 | 2 ,44&53% | | 6 ,42% | 10 ,96&67% |
| 33-1 | 2 ,49&59% | | 6 ,47% | 11 ,63% |
| 33-2 | 2 ,51&47% | | 6 ,55% | 11 ,63% |
| 33-3 | 2 ,48&64% | | 6 ,70% | 11 ,70% |
| 34-1 | 2 ,39&64% | | 6 ,62% | 10 ,87&80% |
| 34-2 | | 5 ,91% | 8 ,80% | 11 ,73% |
| 34-3 | 2 ,50&62% | | 6 ,49% | 11 ,62% |
| 34-4 | | 5 ,88% | 8 ,65% | 9 ,90% |
| 35-1 | 2 ,78&60% | | 6 ,68% | 11 ,76% |
| 35-2 | | 5 ,95% | 8 ,88% | 11 ,72% |
| 35-3 | 2 ,69&58% | | 6 ,70% | 11 ,68% |
| 35-4 | | 5 ,87% | 8 ,82% | 11 ,69% |
| 36-1 | 2 ,63&63% | | 6 ,60% | 11 ,52% |
| 36-2 | 1 ,79% | | 6 ,84% | 11 ,54% |
| 36-3 | | 5 ,91% | 8 ,86% | 10 ,80&60% |
| 36-4 | | 5 ,93% | 8 ,85% | 10 ,78&70% |
| 37-1 | 2 ,63&70% | | 6 ,55% | 11 ,78% |
| 37-2 | | 5 ,92% | 8 ,78% | 10 ,80&69% |
| 37-3 | 2 ,62&61% | | 6 ,54% | 11 ,72% |
| 38-1 | 2 ,58&48% | | 6 ,54% | 11 ,85% |
| 38-2 | | 5 ,81% | | 11 ,74% |
| 38-3 | 2 ,61&47% | | 6 ,46% | 11 ,74% |
| 39-1 | 2 ,37&53% | | 6 ,42% | 10 ,88&74% |
| 39-2 | 2 ,43&54% | | 6 ,43% | 11 ,65% |
| 39-3 | 2 ,59&63% | | 6 ,46% | 11 ,69% |
| 40-1 | 2 ,68&56% | | 6 ,61% | 11 ,81% |
| 40-2 | 2 ,65&47% | | 6 ,54% | 11 ,69% |
| 40-3 | 2 ,48&52% | | 6 ,41% | 11 ,74% |
| 40-4 | | 5 ,92% | 8 ,78% | 11 ,84% |
| 41-1 | 2 ,73&62% | | 6 ,41% | 11 ,67% |
| 41-2 | | 5 ,94% | 8 ,85% | 11 ,59% |
| 41-3 | 2 ,69&68% | | 6 ,45% | 11 ,49% |
| 42-1 | | 5 ,80% | 8 ,90% | 11 ,78% |
| 42-2 | 2 ,62&59% | | 6 ,44% | 11 ,62% |
| 42-3 | 2 ,80&48% | | 6 ,44% | 11 ,79% |
| 43-1 | 2 ,67&69% | | 6 ,44% | 11 ,58% |
| 43-2 | 2 ,63&61% | | 6 ,52% | 11 ,73% |
| 44-1 | 2 ,39&70% | | 6 ,54% | 11 ,72% |
| 45-1 | 2 ,72&72% | | 6 ,64% | 11 ,86% |
| 45-2 | 2 ,48&59% | | 6 ,54% | 11 ,71% |
| 46-1 | 2 ,80&70% | | 6 ,59% | 11 ,62% |
| 46-2 | | 5 ,92% | 8 ,89% | 11 ,50% |
| 46-3 | 2 ,69&62% | | 6 ,46% | 11 ,59% |
| 47-1 | 2 ,49&53% | | 6 ,48% | 11 ,72% |
| 47-2 | 2 ,37&53% | | 6 ,53% | 11 ,73% |
| 48-1 | 2 ,60&62% | | 6 ,52% | 11 ,78% |

The data of the present compounds synthesized above are shown in Table 2. Incidentally, $Z_0$ and $Z_1$ are shown below.

$Z_0$ = :

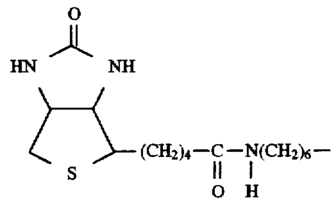

$Z_1$ = :

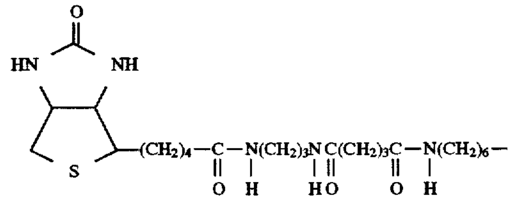

Table 2

Compound 14-1

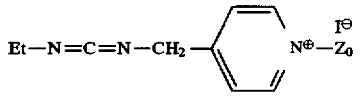

$^1$H-NMR (DMSO-$d_6$) δ=1.20–1.75 (17H,m), 2.02 (2H,t), 2.60 (1H,d), 2.80 (1H,dd), 2.90–3.10 (3H,m), 3.30 (2H,q), 3.60 (2H,t), 4.10 (1H,m), 4.30 (1H,m), 4.65 (2H,s), 6.40 (1H,s), 6.45 (1H,s), 8.00 (2H,d), 8.75 (1H,t), 8.90 (2H,d) IR (KBr) $cm^{-1}$ 3280, 2180, 1645, 1580, 1550

Compound 14-2

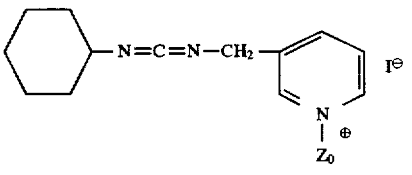

$^1$H-NMR (DMSO-$d_6$) δ=1.20–1.90 (24H,m), 2.01 (2H,t), 2.60 (1H,d), 2.85 (1H,d), 2.90–3.25 (4H,m), 3.65 (2H,t), 4.10 (1H,m), 4.30 (1H,m), 4.40 (2H,s), 6.40 (1H,s), 7.35 (1H,m), 7.60 (1H,d), 7.75 (2H,m), 8.50 (1H,t) IR (KBr) $cm^{-1}$ 3300, 2950, 2180, 1710, 1650, 1586, 1544

Compound 14-3

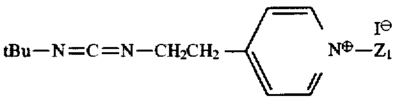

$^1$H-NMR (DMSO-$d_6$) δ=1.14–1.79 (27H,m), 1.93–2.11 (6H, m), 2.57 (1H,d), 2.82 (1H,dd), 2.91–3.26 (9H,m), 3.56 (2H,t), 4.16–4.28 (3H,m), 4.36 (1H,m), 6.37 (1H,s), 6.44 (1H,s), 7.91 (3H,bs), 8.66 (2H,d), 9.13 (2H,d) IR (KBr) $cm^{-1}$ 3310, 2934, 2178, 1703, 1648, 1584, 1546

Compound 14-4

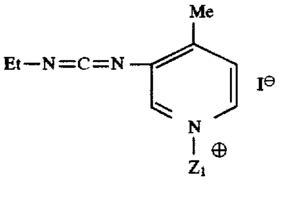

$^1$H-NMR (DMSO-$d_6$) δ1.20–1.85 (21H,m), 1.96–2.09 (6H, m), 2.54 (1H,d), 2.78 (1H,dd), 2.89–3.36 (9H,m), 3.61 (3H,s), 3.66 (2H,t), 4.16 (1H,m), 4.29 (1H,m), 6.34 (1H,s), 6.46 (1H,s), 7.88 (3H,bs), 8.28 (1H,d), 9.01 (1H,d), 9.16 (1H,s) IR (KBr) $cm^{-1}$ 3289, 2211, 1694, 1646, 1594, 1548

Compound 15-1

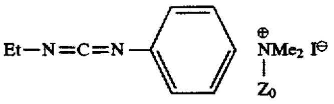

$^1$H-NMR (DMSO-$d_6$) δ=1.21–1.74 (17H,m), 2.01 (2H,t), 2.64 (1H,d), 2.79 (1H,dd), 2.91–3.08 (9H,m), 3.31 (2H,q), 3.62 (2H,t), 4.09 (1H,m), 4.33 (1H,m), 6.43 (1H,s), 6.47 (1H,s), 7.62 (2H,d), 7.84 (2H,d), 8.81 (1H,t) IR (KBr) $cm^{-1}$ 3278, 2212, 1713, 1655, 1601, 1554

Compound 15-2

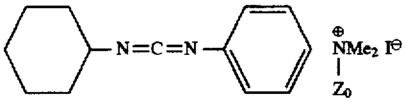

$^1$H-NMR (DMSO-$d_6$) δ=1.21–2.04 (26H,m), 2.60 (1H,d), 2.81 (1H,dd), 2.92–3.31 (4H,m), 3.70 (2H,t), 4.11 (1H,m), 4.26 (1H,m), 4.42 (1H,s), 6.44 (1H,s), 6.47 (1H,s), 7.58 (2H,d), 7.82 (2H,d), 8.85 (1H,t) IR (KBr) $cm^{-1}$ 3274, 2203, 1700, 1658, 1594, 1546

Compound 15-3

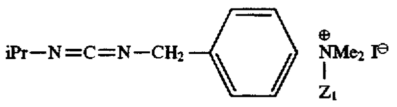

$^1$H-NMR (DMSO-$d_6$) δ=1.11–1.84 (24H,m), 1.95–2.11 (6H, m), 2.68 (1H,d), 2.81 (1H,dd), 2.95–3.36 (8H,m), 3.69 (2H,t), 4.14 (1H,m), 4.34 (1H,m), 4.81 (2H,s), 6.35 (1H,s), 6.46 (1H,s), 7.92 (3H,m), 8.01 (2H,d), 8.86 (2H,d) IR (KBr) $cm^{-1}$ 3284, 2181, 1700, 1643, 1595, 1547

Compound 16-1

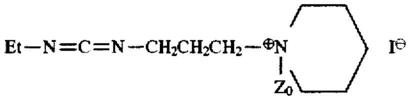

$^1$H-NMR (DMSO-$d_6$) δ=1.14–1.87 (21H,m), 1.96–2.10 (4H,m), 2.56 (1H,d), 2.81 (1H,dd), 2.93–3.36 (5H,m), 3.69–3.81 (10H,m), 4.11 (1H,m), 4.38 (1H,m), 6.40 (1H,s), 6.45 (1H,s), 7.78 (1H,t) IR (KBr) $cm^{-1}$ 3310, 2150, 1700, 1646, 1558

Compound 16-2

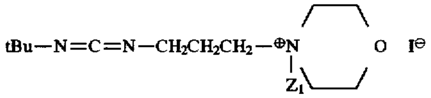

$^1$ H-NMR (DMSO-$D_6$) δ=1.20–2.23 (39H,m), 2.64 (1H,d), 2.79 (1H,dd), 2.95–3.91 (10H,m), 4.16 (1H,m), 4.29 (1H, m), 6.33 (1H,s), 6.42 (1H,s), 7.91 (3H,bs) IR (KBr) $cm^{-1}$ 3329, 2927, 2151, 1705, 1643, 1551, 1122

Compound 17-1

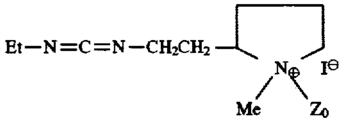

$^1$H-NMR (DMSO-$d_6$) δ=1.15–1.79 (17H,m), 1.94–2.19 (8H,m), 2.56 (1H,d), 2.78 (1H,dd), 2.88–3.34 (8H,m), 3.62 (3H,t), 3.64 (2H,t), 3.87 (2H,t), 4.15 (1H,m), 4.36 (1H,m), 6.40 (1H,s), 6.46 (1H,s), 7.78 (1H,t) IR (KBr) $cm^{-1}$ 32882, 2148, 1693, 1644, 1551

Compound 17-2

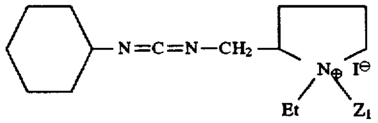

$^1$H-NMR (DMSO-$d_6$) δ=1.11–2.24 (41H,m), 2.58 (1H,d), 2.77 (1H,dd), 2.91–3.32 (13H,m), 3.66 (2H,t), 3.94 (2H,d), 4.11 (1H,m), 4.27 (1H,m), 6.39 (1H,s), 6.47 (1H,s), 7.85 (1H,t) IR (KBr) $cm^{-1}$ 3299, 2981, 2140, 1696, 1652, 1548

Compound 18-1

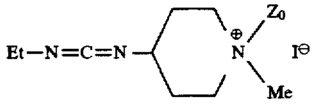

$^1$H-NMR (DMSO-$d_6$) δ=1.21–1.82 (19H,m), 1.92–2.08 (3H,m), 2.58 (1H,d), 2.74 (1H,dd), 2.86–3.31 (5H,m), 3.56–3.69 (9H,m), 4.11 (1H,m), 4.32 (1H,m), 6.35 (1H,s), 6.40 (1H,s), 7.78 (1H,t) IR (KBr) $cm^{-1}$ 3291, 2153, 1701, 1644, 1546

Compound 18-2

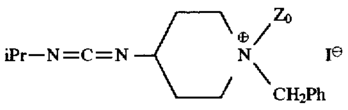

$^1$H-NMR (DMSO-$d_6$) δ=1.09–1.84 (24H,m), 1.96–2.04 (3H,m), 2.58 (1H,d), 2.88 (1H,dd), 2.90–3.36 (4H,m), 3.61–3.79 (8H,m), 4.16 (1H,m), 4.32 (1H,m), 6.40 (1H,s), 6.46 (1H,s), 7.57–7.77 (5H,s), 7.88 (1H,t) IR (KBr) $cm^{-1}$ 3278, 2149, 1701, 1652, 1561, 1544

Compound 18-3

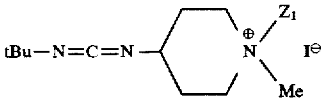

$^1$H-NMR (DMSO-$d_6$) δ=1.14–1.79 (31H,m), 1.96–2.16 (7H,m), 2.64 (1H,d), 2.78 (1H,dd), 2.96–3.27 (7H,m), 3.60–3.69 (9H,m), 4.21 (1H,m), 4.44 (1H,m), 6.45 (1H,s), 6.51 (1H,s), 7.91 (3H,bs) IR (KBr) $cm^{-1}$ 3298, 2927, 2156, 1695, 1652, 1547

Compound 18-4

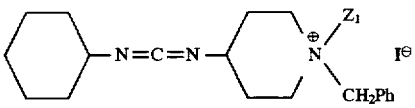

$^1$H-NMR (DMSO-$d_6$) δ=1.14–2.16 (39H,m), 2.62 (1H,d), 2.74 (1H,dd), 2.92–3.24 (8H,m), 3.55–3.87 (8H,m), 4.13 (1H,m), 4.32 (1H,m), 6.34 (1H,s), 6.47 (1H,s), 7.51–7.76 (5H,m), 7.96 (3H,bs) IR (KBr) $cm^{-1}$ 3278, 2911, 2145, 1702, 1648, 1573, 1552

Compound 19-1

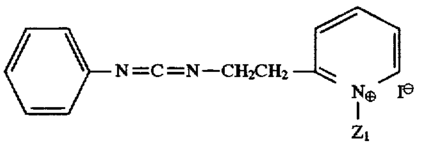

$^1$H-NMR (DMSO-$d_6$) δ=1.21–2.11 (18H,m), 2.42–3.42 (17H,m), 4.21 (1H,m), 4.42 (1H,m), 4.51 (2H,bs), 4.92 (2H,bs), 6.40 (1H,bs), 6.50 (1H,bs), 7.11–7.52 (5H,m), 8.02 (1H,m), 8.05 (1H,d), 8.41 (1H,m), 8.51 (3H,bs), 8.92 (1H,d) IR (KBr) $cm^{-1}$ 3288, 2127, 1701, 1645, 1601, 1582, 1549, 1484

Compound 19-2

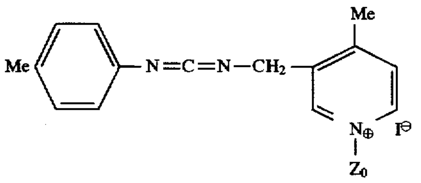

$^1$H-NMR (DMSO-$d_6$) δ=1.21–2.11 (14H,m), 2.32 (3H,s), 2.61 (3H,s), 2.51–3.51 (9H,m), 4.22 (1H,m), 4.44 (1H,m), 4.93 (2H,s), 6.40 (1H,bs), 6.50 (1H,bs), 7.12 (2H,d), 7.33 (2H,d), 8.01 (1H,d), 8.42 (1H,bs), 8.91 (1H,s), 8.98 (1H,d) IR (KBr) $cm^{-1}$ 3286, 2130, 1702, 1644, 1620, 1583, 1544, 1486

Compound 19-3

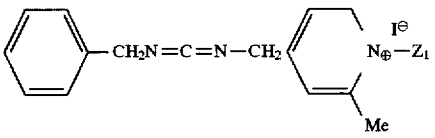

$^1$H-NMR (DMSO-$d_6$) δ=1.21–2.01 (18H,m), 2.54–3.51 (17H,m), 2.62 (3H,s), 4.21 (1H,m), 4.42 (1H,m), 4.81 (2H, s), 4.92 (2H,s), 6.40 (1H,bs), 6.51 (1H,bs), 7.01–7.52 (5H, m), 8.02 (1H,d), 8.13 (1H,s), 8.45 (3H,bs), 8.93 (1H,d) IR (KBr) $cm^{-1}$ 3289, 2127, 1702, 1644, 1601, 1581, 1545, 1485

Compound 19-4

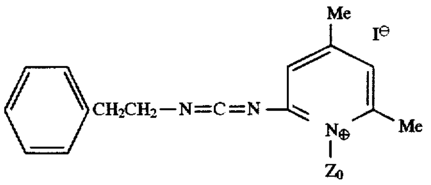

$^1$H-NMR (DMSO-$d_6$) δ=1.22–2.12 (14H,m), 2.42–3.45 (9H,m), 2.61 (3H,s), 2.63 (3H,s), 3.62 (4H,m), 4.23 (1H,m), 4.45 (1H,m), 6.40 (1H,bs), 6.50 (1H,bs), 7.01–7.53 (5H,m), 8.40 (1H,bs), 8.45 (1H,s), 8.55 (1H,s) IR (KBr) $cm^{-1}$ 3288, 2130, 1701, 1644, 1603, 1600, 1582, 1549, 1484

Compound 20-1

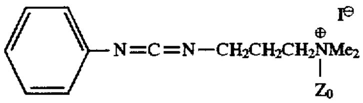

$^1$H-NMR (DMSO-$d_6$) δ=1.21–2.11 (16H,m), 2.52–3.61 (13H,m), 3.25 (6H,s), 4.21 (1H,m), 4.45 (1H,m), 6.40 (1H, bs), 6.50 (1H,bs), 7.04–7.52 (5H,m), 8.42 (1H,bs) IR (KBr) $cm^{-1}$ 3288, 2130, 1702, 1649, 1600, 1545

Compound 20-2

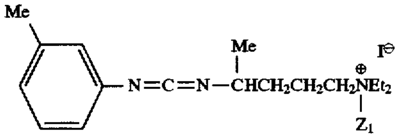

$^1$H-NMR (DMSO-$d_6$) δ=1.21–2.21 (34H,m), 2.56–3.51 (24H,m), 2.65 (3H,s), 4.21 (1H,m), 4.42 (1H,m), 6.40 (1H, bs), 6.50 (1H,bs), 7.01–7.52 (4H,m), 8.40 (3H,bs) IR (KBr) $cm^{-1}$ 3287, 2127, 1701, 1645, 1621, 1548

Compound 20-3

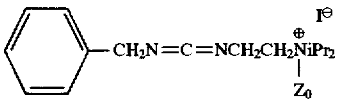

$^1$H-NMR (DMSO-$d_6$) δ=1.12 (12H,d), 1.21–2.11 (14H,m), 2.42–3.41 (15H,m), 4.11 (2H,s), 4.25 (1H,m), 4.42 (1H,m), 6.40 (1H,bs), 6.51 (1H,bs), 7.01–7.54 (5H,m), 8.50 (1H,bs) IR (KBr) $cm^{-1}$ 3286, 2125, 1702, 1646, 1600, 1548

Compound 20-4

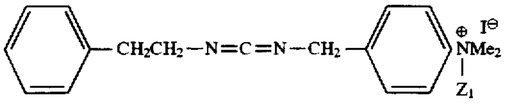

$^1$H-NMR (DMSO-$d_6$) δ=1.22–2.11 (18H,m), 2.56–3.45 (21H,m), 4.22 (1H,m), 4.45 (1H,m), 4.85 (6H,s), 4.95 (2H, s), 6.40 (1H,bs), 6.51 (1H,bs), 7.11–7.62 (9H,m), 8.40 (3H,bs) IR (KBr) cm$^{-1}$ 3286, 2131, 1703, 1646, 1621, 1601, 1549

Compound 21-1

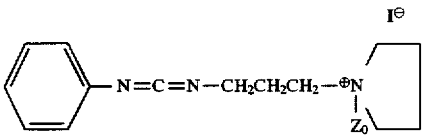

$^1$H-NMR (DMSO-$d_6$) δ=1.21–2.11 (20H,m), 2.54–3.51 (17H,m), 4.21 (1H,m), 4.42 (1H,m), 6.40 (1H,bs), 6.51 (1H,bs), 7.01–7.73 (5H,m), 8.41 (1H,bs) IR (KBr) cm$^{-1}$ 3286, 2131, 1702, 1647, 1602, 1548

Compound 21-2

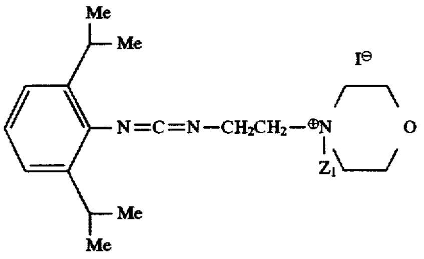

$^1$H-NMR (DMSO-$d_6$) δ=1.22 (12H,d), 1.21–2.01 (18H,m), 2.41–3.42 (23H,m), 4.01 (4H,bs), 4.22 (1H,m), 4.45 (1H,m), 6.40 (1H,bs), 6.51 (1H,bs), 7.01–7.61 (3H,m), 8.40 (1H,bs) IR (KBr) cm$^{-1}$ 3288, 2124, 1703, 1645, 1580, 1548, 1101

Compound 21-3

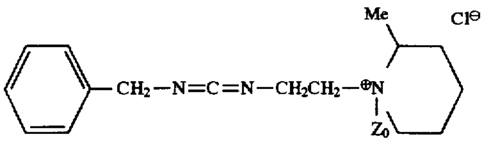

$^1$H-NMR (DMSO-$d_6$) δ=1.43 (3H,d), 1.22–2.12 (20H,m), 2.45–3.52 (16H,m), 4.21 (1H,m), 4.45 (2H,s), 6.41 (1H,bs), 6.52 (1H,bs), 7.01–7.52 (5H,m), 8.50 (1H,bs) IR (KBr) cm$^{-1}$ 3289, 2126, 1703, 1649, 1601, 1548

Compound 21-4

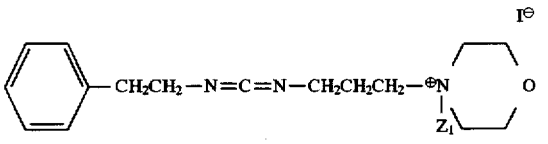

$^1$H-NMR (DMSO-$d_6$) δ=1.11–2.21 (20H,m), 2.42–3.41 (29H,m), 4.02 (4H,bs), 4.21 (1H,m), 4.44 (1H,m), 6.40 (1H,bs), 6.51 (1H,bs), 7.01–7.52 (5H,m), 8.50 (3H,bs) IR (KBr) cm$^{-1}$ 3289, 2127, 1701, 1648, 1602, 1545, 1112

Compound 22-1

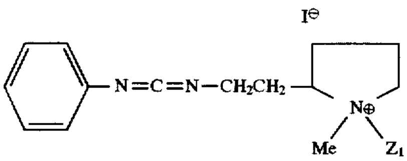

$^1$H-NMR (DMSO-$d_6$) δ=1.21–2.21 (24H,m), 2.62–3.62 (22H,m), 3.22 (3H,s), 4.21 (1H,m), 4.42 (1H,m), 6.40 (1H, bs), 6.50 (1H,bs), 7.01–7.61 (5H,m), 8.41 (3H,bs) IR (KBr) cm$^{-1}$ 3285, 2127, 1701, 1646, 1601, 1548

Compound 22-2

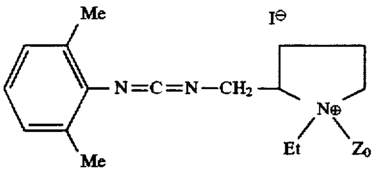

$^1$H-NMR (DMSO-$d_6$) δ=1.12–2.21 (21H,m), 2.42–3.41 (14H,m), 2.32 (6H,s), 3.52 (2H,q), 4.21 (1H,m), 4.42 (1H, m), 6.40 (1H,bs), 6.51 (1H,bs), 7.01–7.53 (3H,m), 8.42 (1H,bs) IR (KBr) cm$^{-1}$ 3286, 2127, 1703, 1646, 1581, 1549

Compound 22-3

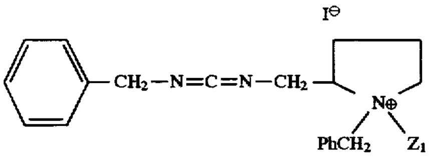

$^1$H-NMR (DMSO-$d_6$) δ=1.21–2.11 (22H,m), 2.62–3.61 (22H,m), 4.22 (1H,m), 4.45 (1H,m), 4.51 (2H,s), 4.82 (2H, s), 6.41 (1H,bs), 6.51 (10H,m), 8.40 (3H,bs) IR (KBr) cm$^{-1}$ 3288, 2127, 1702, 1645, 1602, 1549

Compound 22-4

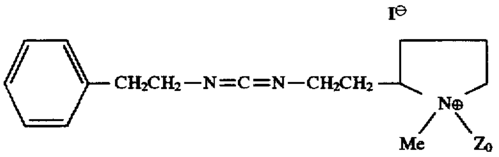

$^1$H-NMR (DMSO-$d_6$) δ=1.21–2.15 (20H,m), 2.45–3.61 (18H,m), 3.22 (3H,s), 4.21 (1H,m), 4.42 (1H,m), 6.40 (1H, bs), 6.51 (1H,bs), 7.01–7.63 (5H,m), 8.42 (1H,bs) IR (KBr) cm$^{-1}$ 3287, 2126, 1703, 1646, 1601, 1548

Compound 23-1

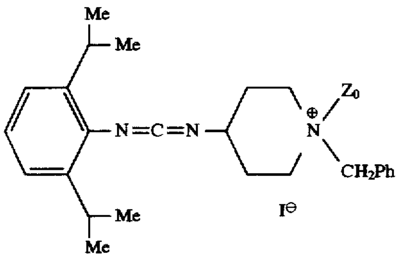

$^1$H-NMR (DMSO-$d_6$) δ=1.25 (12H, d), 1.26–2.31 (18H, m), 2.62–3.65 (16H,m), 4.21 (1H,m), 4.42 (1H,m), 4.53

(2H,s), 6.41 (1H,bs), 6.52 (1H,bs), 7.01–7.72 (8H,m), 8.40 (1H,bs) IR (KBr) $cm^{-1}$ 3286, 2126, 1702, 1646, 1602, 1581, 1548

Compound 23-2

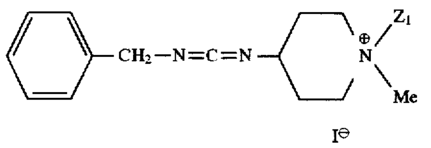

$^1$H-NMR (DMSO-$d_6$) δ=1.12–2.31 (22H,m), 2.42–3.71 (22H,m), 3.24 (3H,s), 4.21 (1H,m), 4.42 (1H,m), 4.82 (2H, s), 6.41 (1H,bs), 6.52 (1H,bs), 7.01–7.62 (5H ,m), 8.41 (3H,bs) IR (KBr) $cm^{-1}$ 3286, 2131, 1703, 1645, 1602, 1548

Compound 24-1

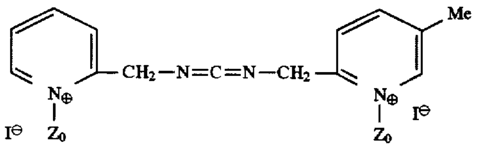

$^1$H-NMR (DMSO-$d_6$) δ=1.12–2.21 (28H,m), 2.60 (3H,s), 2.61–3.62 (18H,m), 4.21 (2H,m), 4.42 (2H,m), 4.92 (2H,s), 4.95 (2H,s), 6.40 (2H,bs), 6.41 (2H,bs), 8.01–9.02 (9H,m) IR (KBr) $cm^{-1}$ 3286, 2127, 1702, 1644, 1598, 1582, 1549, 1484

Compound 24-2

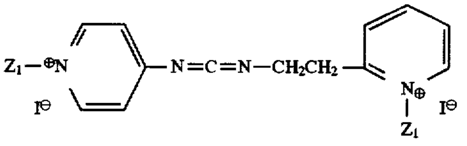

$^1$H-NMR (DMSO-$d_6$) δ=1.12–2.21 (36H,m), 2.52–3.52 (38H,m), 4.21 (2H,m), 4.42 (2H,m), 6.40 (2H,bs), 6.51 (2H,bs), 8.12–9.11 (14H,m) IR (KBr) $cm^{-1}$ 3288, 2127, 1702, 1644, 1599, 1581, 1548, 1485

Compound 24-3

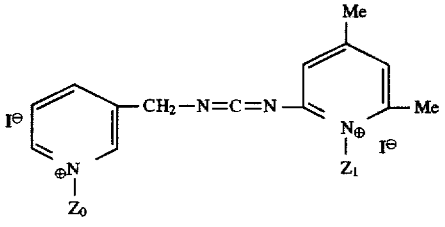

$^1$H-NMR (DMSO-$d_6$) δ=1.21–2.22 (28H,m), 2.62 (3H,s), 2.65 (3H,s), 2.67–3.61 (18H,m), 4.21 (2H,m), 4.42 (2H,m), 4.92 (2H,s), 6.40 (2H,bs), 6.51 (2H,bs), 8.11–9.12 (8H,m) IR (KBr) $cm^{-1}$ 3288, 2124, 1702, 1644, 1599, 1581, 1548, 1486

Compound 24-4

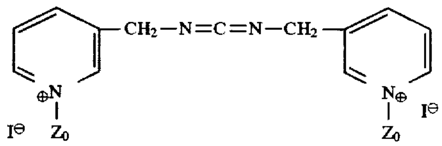

$^1$H-NMR (DMSO-$d_6$) δ=1.10–1.80 (28H,m), 2.05 (4H,t), 2.55 (2H,d), 2.85 (2H,dd), 2.95–3.15 (6H,m), 3.30 (4H,t), 4.15 (2H,m), 4.35 (2H,m), 4.40 (4H,s), 6.35 (2H,s), 6.40 (2H,s), 7.35 (2H,m), 7.65 (2H,d), 7.70–7.80 (4H,m), 8.50 (2H,m) IR (KBr) $cm^{-1}$ 3340, 3280, 3090, 2935, 2130, 1690, 1640, 1550, 1460

Compound 25-1

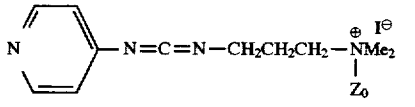

$^1$H-NMR (DMSO-$d_6$) δ=1.21–2.21 (16H,m), 2.61–3.42 (13H,m), 3.22 (6H,s), 4.21 (1H,m), 4.42 (1H,m), 6.41 (1H, bs), 6.52 (1H,bs), 7.12 (2H,d), 8.38 (2H,d), 8.50 (1H,bs) IR (KBr) $cm^{-1}$ 3286, 2127, 1703, 1644, 1598, 1582, 1548, 1485

Compound 25-2

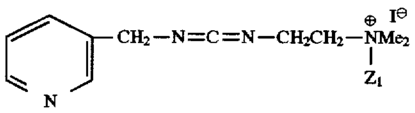

$^1$H-NMR (DMSO-$d_6$) δ=1.21–2.21 (18H,m), 2.62–3.61 (21H,m), 3.24 (6H,s), 4.21 (1H,m), 4.42 (1H,m), 4.45 (2H, s), 6.40 (1H,bs), 6.51 (1H,bs), 7.21 (1H,t), 7.52 (1H,d), 8.41 (1H,s), 8.51 (1H,bs), 8.56 (1H,d) IR (KBr) $cm^{-1}$ 3288, 2131, 1702, 1645, 1598, 1581, 1548, 1484

Compound 25-3

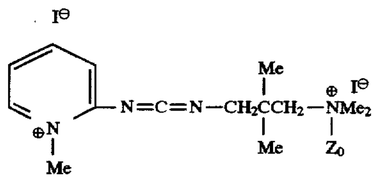

$^1$H-NMR (DMSO-$d_6$) δ=1.12 (6H,s), 1.14–2.25 (14H,m), 2.61–3.62 (13H,m), 3.21 (6H,s), 4.25 (1H,m), 4.44 (1H,m), 4.51 (3H,s),6.40 (1H,bs), 6.51 (1H,bs), 8.01 (1H,d), 8.11 (1H,m), 8.42 (1H,bs), 8.53 (1H,m), 8.91 (1H,d) IR (KBr) $cm^{-1}$ 3288, 2128, 1703, 1645, 1598, 1581, 1549, 1484

Compound 25-4

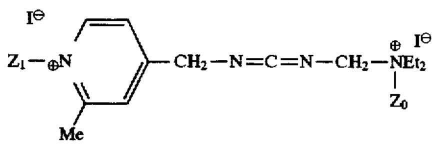

$^1$H-NMR (DMSO-$d_6$) δ=1.22 (6H,t), 1.23–2.21 (32H,m), 2.61–3.62 (26H,m), 3.51 (4H,q), 4.21 (2H,m), 4.42 (2H,m), 4.52 (2H,s), 4.57 (2H,s), 4.73 (3H,s), 6.40 (2H,bs), 6.51 (2H,bs), 8.01 (1H,d), 8.11 (1H,s), 8.40 (4H,bs), 8.93 (1H,d) IR (KBr) $cm^{-1}$ 3287, 2131, 1701, 1599, 1582, 1549, 1485

Compound 25-5

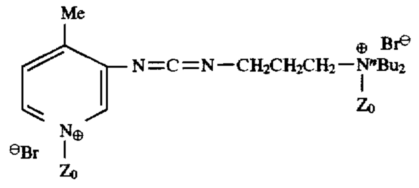

$^1$H-NMR (DMSO-$d_6$) δ=0.92 (6H,t), 1.12–2.35 (38H,m), 2.61 (3H,s), 2.62–3.61 (26H,m), 4.21 (2H,m), 4.42 (2H,m), 6.40 (2H,bs), 6.51 (2H,bs), 8.01 (1H,d), 8.42 (2H,bs), 8.91 (1H,d), 8.98 (1H,s) IR (KBr) $cm^{-1}$ 3286, 2130, 1703, 1644, 1599, 1581, 1545, 1484

Compound 25-6

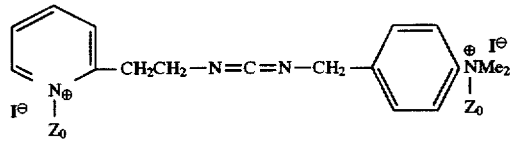

$^1$H-NMR (DMSO-$d_6$) δ=1.12–2.21 (28H,m), 2.41–3.72 (22H,m), 3.52 (6H,s), 4.21 (2H,m), 4.42 (2H,m), 4.92 (2H, s), 6.40 (2H,bs), 6.51 (2H,bs), 7.61 (2H,d), 7.82 (2H,d), 8.01 (1H,d), 8.11 (1H,m), 8.42 (2H,bs), 8.53 (1H,m), 8.91 (1H,d) IR (KBr) $cm^{-1}$ 3287, 2131, 1702, 1646, 1598, 1582, 1545, 1484

Compound 25-7

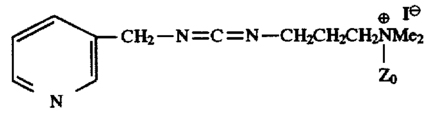

$^1$H-NMR (DMSO-$d_6$) δ=1.25–1.70 (14H,m), 1.75–1.90 (2H,m), 2.05 (2H,t), 2.55 (1H,d), 2.85 (1H,dd), 3.03 (6H,s), 3.05–3.40 (9H,m), 4.15 (1H,m), 4.35 (1H,m), 4.50 (2H,s), 6.40 (1H,s), 6.45 (1H,s), 7.45 (1H,q), 7.70–7.80 (2H,m), 7.95 (1H,s), 8.50 (1H,t) IR (KBr) $cm^{-1}$ 3280, 2931, 2130, 1700, 1650, 1540, 1455, 1430

Compound 26-1

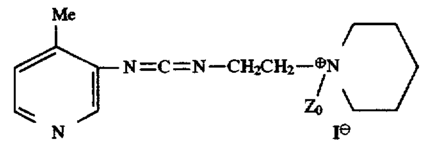

$^1$H-NMR (DMSO-$d_6$) δ=1.21–2.21 (20H,m), 2.62 (3H,s), 2.64–3.61 (17H,m), 4.21 (1H,m), 4.42 (1H,m), 6.40 (1H,bs), 6.51 (1H,bs), 7.11 (1H,d), 7.52 (1H,s), 8.41 (1H,bs), 8.52 (1H,d) IR (KBr) $cm^{-1}$ 3287, 2130, 1703, 1645, 1597, 1581, 1548, 1483

Compound 26-2

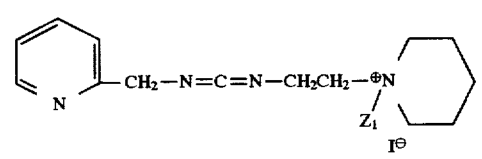

$^1$H-NMR (DMSO-$d_6$) δ=1.12–2.21 (22H,m), 2.52–3.61 (24H,m), 4.22 (1H,m), 4.42 (1H,m), 4.51 (2H,s), 6.40 (1H, bs), 6.51 (1H,bs), 7.01 (1H,d), 7.12 (1H,m), 7.52 (1H,m), 8.41 (1H,bs), 8.52 (1H,d) IR (KBr) $cm^{-1}$ 3287, 2131, 1704, 1645, 1600, 1581, 1549, 1484

Compound 26-3

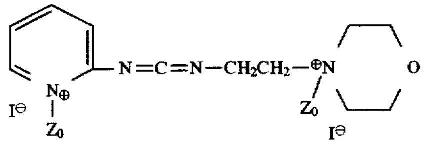

$^1$H-NMR (DMSO-$d_6$) δ=1.12–2.21 (28H,m), 2.61–3.52 (26H,m), 4.02 (4H,bs), 4.22 (2H,m), 4.44 (2H,m), 6.40 (2H,bs), 6.51 (2H,bs), 8.01 (1H,d), 8.12 (1H,m), 8.42 (2H, bs), 8.56 (1H,m), 8.98 (1H,d) IR (KBr) $cm^{-1}$ 3288, 2126, 1702, 1644, 1579, 1551, 1483, 1105

Compound 26-4

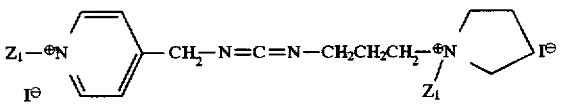

$^1$H-NMR (DMSO-$d_6$) δ=1.21–2.21 (42H,m), 2.56–3.51 (42H,m), 4.21 (2H,m), 4.44 (2H,m), 4.85 (2H,s), 6.40 (2H, bs), 6.51 (2H,bs), 8.01 (2H,d), 8.41 (6H,bs), 8.92 (2H,d) IR (KBr) $cm^{-1}$ 3286, 2131, 1702, 1644, 1598, 1581, 1549, 1485

Compound 26-5

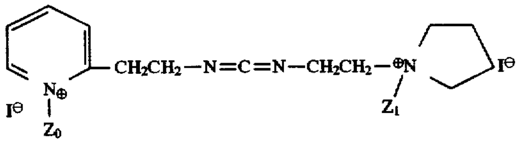

$^1$H-NMR (DMSO-$d_6$) δ=1.22–2.23 (36H,m), 2.61–3.62 (38H,m), 4.21 (2H,m), 4.42 (2H,m), 6.40 (2H,bs), 6.51 (2H,bs), 8.01 (1H,d), 8.12 (1H,m), 8.42 (4H,bs), 8.53 (1H, m), 8.98 (1H,d) IR (KBr) $cm^{-1}$ 3280, 2130, 1700, 1645, 1601, 1581, 1550, 1483

Compound 27-1

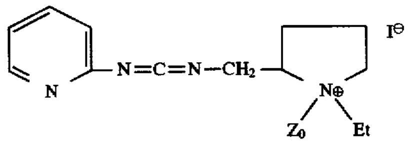

$^1$H-NMR (DMSO-$d_6$) δ=1.21–2.02 (18H,m), 1.42 (3H,t), 2.21–3.42 (16H,m), 4.22 (1H,m), 4.41 (1H,m), 6.41 (1H,bs), 6.51 (1H,bs), 7.11 (2H,m), 7.51 (1H,dd), 8.42 (1H,bs), 8.51 (1H,d) IR (KBr) $cm^{-1}$ 3290, 2131, 1703, 1644, 1601, 1581, 1549, 1488

Compound 27-2

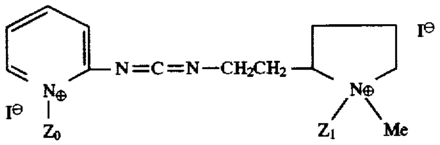

$^1$H-NMR (DMSO-$d_6$) δ=1.21–2.02 (38H,m), 2.31–3.33 (31H,m), 3.51 (3H,s), 4.21 (2H,m), 4.42 (2H,m), 6.41 (2H, bs), 6.52 (2H,bs), 7.21 (1H,dd), 7.42 (1H,d), 8.42 (2H,m), 8.45 (4H,bs) IR (KBr) $cm^{-1}$ 3289, 2130, 1701, 1645, 1599, 1581, 1547, 1480

Compound 27-3

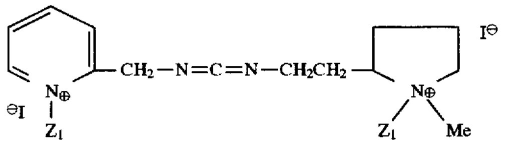

$^1$H-NMR (DMSO-$d_6$) δ=1.22–1.91 (42H,m), 2.31–3.13 (39H,m), 3.51 (3H,s), 4.22 (2H,m), 4.42 (2H,m), 4.91 (2H, s), 6.41 (2H,bs), 6.51 (2H,bs), 7.13 (2H,m), 7.51 (1H,dd), 8.51 (1H,d), 8.61 (6H,bs) IR (KBr) $cm^{-1}$ 3286, 2130, 1702, 1642, 1601, 1586, 1548, 1483

Compound 28-1

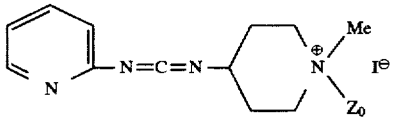

$^1$H-NMR (DMSO-$d_6$) δ=1.21–1.92 (18H,m), 2.31–3.03 (14H,m), 3.52 (3H,s), 4.22 (1H,m), 4.44 (1H,m), 6.41 (1H, bs), 6.51 (1H,bs), 7.12 (2H,m), 7.52 (1H,dd), 8.51 (1H,d), 8.62 (1H,bs) IR (KBr) $cm^{-1}$ 3291, 2124, 1701, 1645, 1601, 1581, 1549, 1486

Compound 28-2

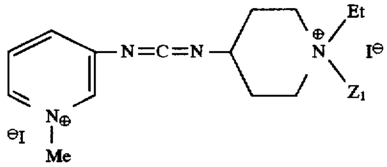

$^1$H-NMR (DMSO-$d_6$) δ=1.21–1.92 (25H,m), 2.32–3.13 (24H,m), 4.22 (1H,m), 4.31 (3H,s), 4.41 (1H,m), 6.41 (1H, bs), 6.51 (1H,bs), 7.21 (1H,dd), 7.43 (1H,d), 8.41 (2H,m), 8.51 (3H,bs) IR (KBr) $cm^{-1}$ 3291, 2125, 1702, 1644, 1600, 1582, 1548, 1485

Compound 28-3

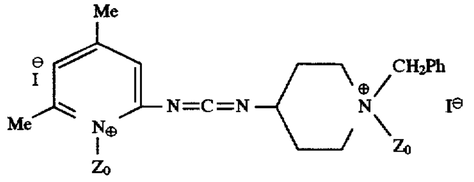

$^1$H-NMR (DMSO-$d_6$) δ=1.21–1.92 (32H,m), 2.32–3.11 (23H,m), 2.31 (3H,s), 2.52 (3H,s), 4.22 (2H,m), 4.41 (2H, m), 5.11 (2H,s), 6.41 (2H,bs), 6.52 (2H,bs), 7.01–7.52 (5H,m), 8.01 (1H,s), 8.11 (1H,s), 8.41 (2H,bs) IR (KBr) $cm^{-1}$ 3287, 1231, 1704, 1645, 1603, 1597, 1581, 1548, 1485

Compound 29-1

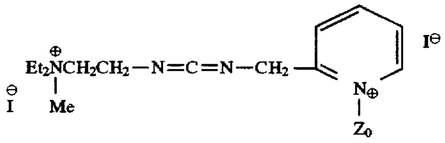

$^1$H-NMR (DMSO-$d_6$) δ=1.21–1.92 (20H,m), 2.34–3.21 (17H,m), 3.51 (3H,s), 4.22 (1H,m), 4.41 (1H,m), 4.91 (2H, s), 6.41 (1H,bs), 6.51 (1H,bs), 7.12 (2H,m), 7.51 (1H,dd), 8.51 (1H,d), 8.61 (1H,bs) IR (KBr) $cm^{-1}$ 3292, 2132, 1703, 1644, 1601, 1581, 1549, 1484

Compound 29-2

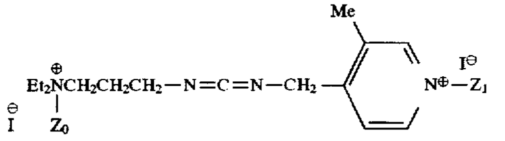

$^1$H-NMR (DMSO-$d_6$) δ=1.21–1.92 (40H,m), 2.31–3.43 (34H,m), 2.61 (3H,s), 4.22 (2H,m), 4.41 (2H,m), 6.41 (2H, bs), 6.51 (2H,bs), 8.01 (1H,d), 8.41 (4H,bs), 8.91 (1H,d), 8.97 (1H,s) IR (KBr) $cm^{-1}$ 3288, 2125, 1702, 1644, 1601, 1581, 1549, 1484

Compound 29-3

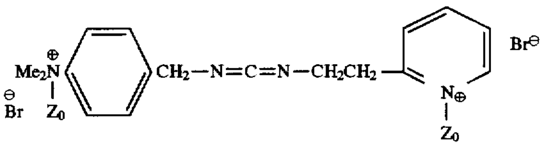

$^1$H-NMR (DMSO-$d_6$) δ=1.21–1.92 (28H,m), 2.31–3.43 (22H,m), 3.51 (6H,s), 4.22 (2H,m), 4.41 (2H,m), 4.91 (2H, s), 6.41 (2H,bs), 6.51 (2H,bs), 7.11–7.82 (6H,m), 8.01 (1H,s), 8.42 (2H,bs), 8.91 (1H,s) IR (KBr) $cm^{-1}$ 3288, 2124, 1703, 1645, 1622, 1601, 1581, 1548, 1486

Compound 29-4

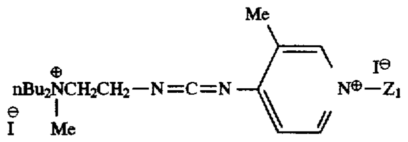

$^1$H-NMR (DMSO-$d_6$) δ=0.91 (6H,t), 1.21–1.92 (26H,m), 2.31–3.43 (25H,m), 2.61 (3H,s), 3.51 (3H,s), 4.22 (1H,m), 4.44 (1H,m), 6.41 (1H,bs), 6.51 (1H,bs), 8.02 (1H,d), 8.42 (3H,bs), 8.92 (1H,d), 8.98 (1H,s) IR (KBr) $cm^{-1}$ 3288, 2130, 1702, 1645, 1601, 1581, 1549, 1485

Compound 30-1

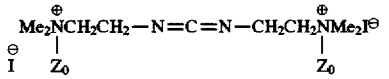

$^1$H-NMR (DMSO-$d_6$) δ=1.21–1.92 (28H,m), 2.21–3.23 (26H,m), 3.52 (12H,s), 4.22 (2H,m), 4.41 (2H,m), 6.42 (2H,bs), 6.52 (2H,bs), 8.41 (2H,bs) IR (KBr) $cm^{-1}$ 3288, 2129, 1703, 1644, 1548

Compound 30-2

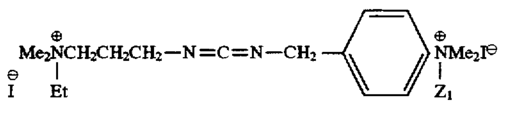

$^1$H-NMR (DMSO-$d_6$) δ=1.21–1.92 (23H,m), 2.31–3.22 (23H,m), 3.52 (6H,s), 4.22 (1H,m), 4.43 (1H,m), 4.81 (2H, s), 4.92 (6H,s)6.41 (1H,bs), 6.52 (1H,bs), 7.62 (2H,dd), 7.83 (2H,dd), 8.42 (3H,bs) IR (KBr) $cm^{-1}$ 3288, 2130, 1702, 1645, 1621, 1548

Compound 30-3

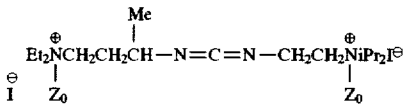

$^1$H-NMR (DMSO-$d_6$) δ=1.21 (12H,d), 1.21–1.92 (41H,m), 2.31–3.14 (31H,m), 4.23 (2H,m), 4.42 (2H,m), 6.41 (2H,bs), 6.51 (2H,bs), 8.42 (2H,bs) IR (KBr) $cm^{-1}$ 3288, 2131, 1703, 1644, 1549

Compound 30-4

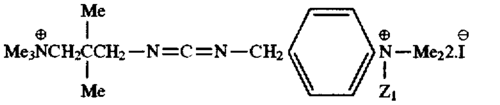

$^1$H-NMR (DMSO-$d_6$) δ=1.21 (6H,s), 1.21–1.92 (18H,m), 2.22–3.41 (21H,m), 3.51 (6H,s), 4.23 (1H,m), 4.42 (1H,m), 4.71 (2H,s), 4.92 (9H,s), 6.41 (1H,m), 6.52 (1H,m), 7.62 (2H,d), 7.81 (2H,d), 8.42 (3H,bs) IR (KBr) $cm^{-1}$ 3288, 2130, 1702, 1644, 1621, 1548

Compound 30-5

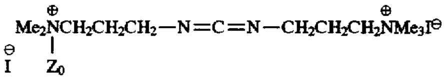

$^1$H-NMR (DMSO-$d_6$) δ1.30–2.10 (18H,m), 2.15 (2H,t), 2.65 (1H,d), 2.90 (1H,dd), 3.03 (6H,s), 3.05 (9H,s), 3.05–3.55 (13H,m), 4.30 (1H,m), 4.50 (1H,m) IR (KBr) $cm^{-1}$ 3410, 3255, 2930, 2130, 1685, 1640, 1545, 1460

Compound 30-6

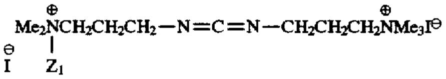

$^1$H-NMR (DMSO-$d_6$) δ=1.20–2.10 (28H,m), 2.55 (1H,d), 2.80 (1H,dd), 2.95–3.20 (25H,m), 3.25–3.45 (7H,m), 4.15 (1H,m), 4.35 (1H,m), 6.35 (1H,s), 6.40 (1H,s), 7.75 (3H, bs) IR (KBr) $cm^{-1}$ 3410, 3260, 2940, 2130, 1690, 1645, 1545, 1465

Compound 30-7

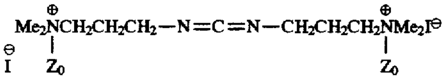

$^1$H-NMR (DMSO-$d_6$) δ=1.25–1.80 (28H,m), 1.85–2.00 (4H,m), 2.15 (4H,t), 2.60 (2H,d), 2.85 (2H,dd), 3.05 (12H,s), 3.05–3.45 (14H,m), 4.25 (2H,m), 4.45 (2H,m) IR (KBr) $cm^{-1}$ 3420, 3260, 2932, 2130, 1690, 1640, 1550, 1460

Compound 30-8

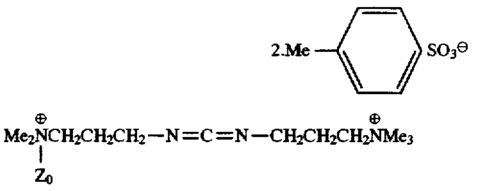

$^1$H-NMR (DMSO-$d_6$) δ=1.20–1.70 (14H,m), 1.80–1.95 (4H,m), 2.05 (2H,t), 2.30 (3H,s), 2.55 (1H,d), 2.80 (1H,dd), 3.00 (6H,s), 3.05 (9H,s), 3.00–3.10 (4H,m), 3.20–3.40 (9H, m), 4.15 (1H,m), 4.30 (1H,m), 6.40 (1H,s) 6.45 (1H,s), 7.15 (2H,d), 7.50 (2H,d), 7.80 (1H,t) IR (KBr) $cm^{-1}$ 3450, 3290, 2930, 2130, 1695, 1654, 1212, 1190, 1120, 1030, 1010, 680

Compound 31-1

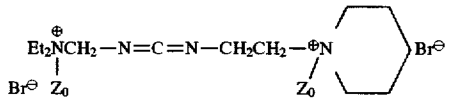

$^1$H-NMR (DMSO-$d_6$) δ=1, 22–1.92 (40H,m), 2.21–3.57 (30H,m), 4.24 (2H,m), 4.42 (2H,m), 4.81 (2H,s), 6.41 (2H, bs), 6.52 (2H,bs), 8.42 (2H,bs) IR (KBr) $cm^{-1}$ 3290, 2131, 1703, 1644, 1549

Compound 31-2

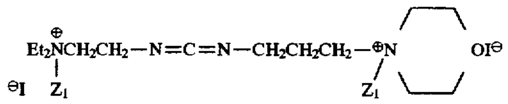

$^1$H-NMR (DMSO-$d_6$) δ=1.26–1.92 (38H,m), 2.31–3.55 (50H,m), 4.01 (4H,bs), 4.27 (2H,m), 4.42 (2H,m), 6.41 (2H,bs), 6.51 (2H,bs), 8.42 (6H,bs) IR (KBr) $cm^{-1}$ 3288, 2125, 1702, 1644, 1548, 1101

Compound 31-3

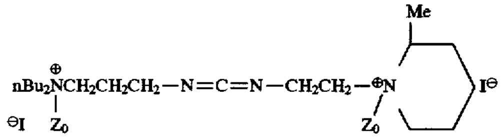

$^1$H-NMR (DMSO-$d_6$) δ=0.92 (6H,t), 1.21–2.15 (47H,m), 2.31–3.54 (33H,m), 4.22 (2H,m), 4.43 (2H,m), 6.41 (2H,bs), 6.52 (2H,bs), 8.43 (2H,bs) IR (KBr) $cm^{-1}$ 3291, 2126, 1703, 1645, 1549

Compound 31-4

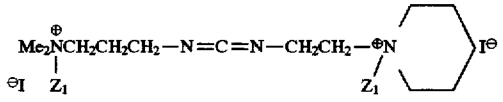

$^1$H-NMR (DMSO-$d_6$) δ=1.21–2.22 (44H,m), 2.51–3.55 (46H,m), 3.51 (6H,s), 4.26 (2H,m), 4.42 (2H,m), 6.42 (2H, bs), 6.51 (2H,bs), 8.43 (6H,bs) IR (KBr) $cm^{-1}$ 3289, 2131, 1701, 1645, 1548

Compound 31-5

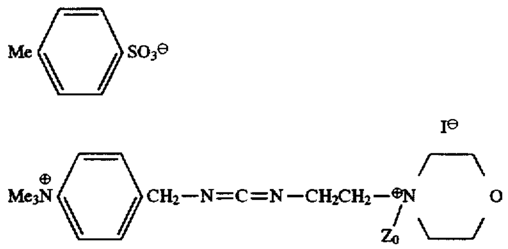

$^1$H-NMR (DMSO-$d_6$) δ=1.21–1.78 (14H,m), 1.84–1.96 (2H,m), 2.05 (2H,t), 2.32 (3H,s), 2.41 (4H,bs), 2.57 (1H,d), 2.76 (1H,dd), 3.08 (9H,s), 3.04–3.53 (7H,m), 3.62 (4H,bs), 4.15 (1H,m), 4.32 (1H,m), 4.61 (2H,s), 4.78 (2H,t), 6.34 (1H,s), 6.45 (1H,s), 7.14 (2H,d), 7.50 (2H,d), 7.62 (2H,d), 7.83 (2H,d), 8.14 (1H,t) IR (KBr) $cm^{-1}$ 3450, 3300, 2930, 2135, 1695, 1650, 1210, 1190, 1120, 1030, 680

Compound 32-1

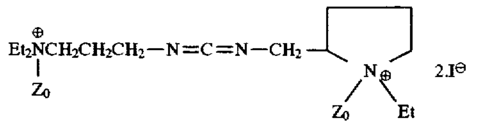

$^1$H-NMR (DMSO-$d_6$) δ=1.21–2.32 (43H,m), 2.51–3.54 (33H,m), 4.22 (2H,m), 4.43 (2H,m), 6.41 (2H,bs), 6.52 (2H,bs), 8.41 (2H,bs) IR (KBr) $cm^{-1}$ 3289, 2129, 1704, 1645, 1548

Compound 32-2

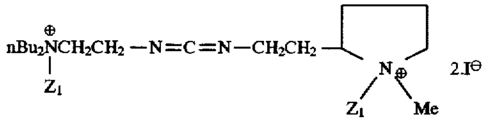

$^1$H-NMR (DMSO-$d_6$) δ=0.92 (6H,t), 1.21–2.32 (50H,m), 2.51–3.65 (47H,m), 3.51 (3H,s), 4.26 (2H,m), 4.42 (2H,m), 6.41 (2H,bs), 6.51 (2H,bs), 8.45 (6H,bs) IR (KBr) $cm^{-1}$ 3291, 2131, 1704, 1645, 1549

Compound 32-3

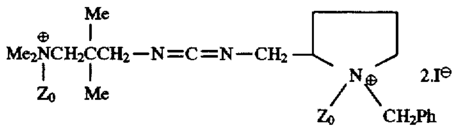

$^1$H-NMR (DMSO-$d_6$) δ=1.19 (6H,s), 1.21–2.32 (32H,m), 2.51–3.54 (27H,m), 3.52 (6H,s), 4.24 (2H,m), 4.42 (2H,m), 5.11 (2H,s), 6.41 (2H,bs), 6.52 (2H,bs), 8.45 (2H,bs) IR (KBr) $cm^{-1}$ 3289, 2125, 1701, 1644, 1602, 1549

Compound 32-4

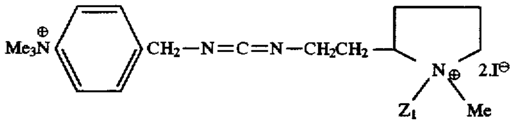

$^1$H-NMR (DMSO-$d_6$) δ=1.22–2.35 (24H,m), 2.56–3.54 (22H,m), 3.52 (3H,s), 4.22 (1H,m), 4.43 (1H,m), 4.83 (2H, s), 4.92 (6H,s), 6.41 (1H,bs), 6.52 (1H,bs), 7.61 (2H,d), 7.82 (2H,d), 8.45 (3H,bs) IR (KBr) $cm^{-1}$ 3291, 2130, 1704, 1645, 1621, 1549

Compound 33-1

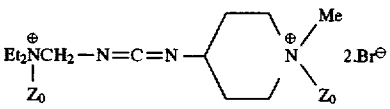

$^1$H-NMR (DMSO-$d_6$) δ=1.22–2.34 (38H,m), 2.51–3.52 (27H,m), 3.53 (3H,s), 4.25 (2H,m), 4.42 (2H,m), 4.82 (2H, s), 6.41 (2H,bs), 6.52 (2H,bs), 8.42 (2H,bs) IR (KBr) $cm^{-1}$ 3291, 2128, 1702, 1645, 1549

Compound 33-2

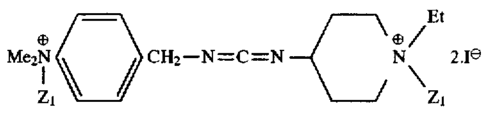

$^1$H-NMR (DMSO-$d_6$) δ=1.22–2.32 (43H,m), 2.56–3.63 (41H,m), 4.24 (2H,m), 4.42 (2H,m), 4.72 (2H,s), 4.83 (6H, s), 6.41 (2H,bs), 6.52 (2H,bs), 7.61 (2H,d), 7.82 (2H,d), 8.43 (6H,bs) IR (KBr) $cm^{-1}$ 3288, 2125, 1705, 1646, 1621, 1548

Compound 33-3

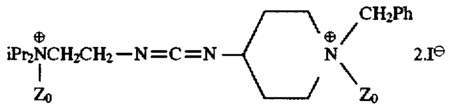

$^1$H-NMR (DMSO-$d_6$) δ=1.21 (6H,d), 1.21–2.33 (32H,m), 2.56–3.52 (29H,m), 4.22 (2H,m), 4.44 (2H,m), 5.12 (2H,s), 6.40 (2H,bs), 6.51 (2H,bs), 7.01–7.55 (5H,m), 8.41 (2H,bs) IR (KBr) $cm^{-1}$ 3291, 2130, 1701, 1645, 1601, 1545

Compound 34-1

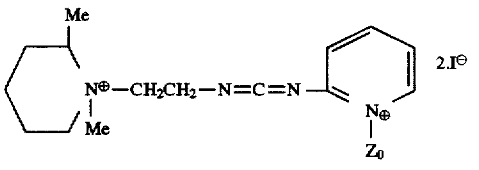

$^1$H-NMR (DMSO-$d_6$) δ=1.21–2. 32 (23H,m), 2.56–3.53 (16H,m), 3.52 (3H,s), 4.22 (1H,m), 4.41 (1H,m), 6.41 (1H, bs), 6.50 (1H,bs), 8.04 (2H,m), 8.41 (1H,bs), 8.52 (1H,m), 8.91 (1H,d) IR (KBr) $cm^{-1}$ 3290, 2129, 1702, 1644, 1601, 1584, 1549, 1484

Compound 34-2

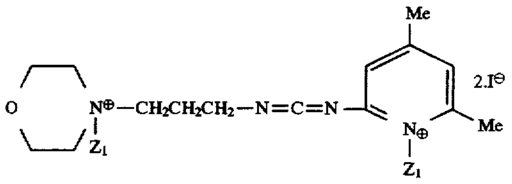

$^1$H-NMR (DMSO-$d_6$) δ=1.21–2.36 (38H,m), 2.62–3.62 (42H,m), 2.61 (3H,s), 2.82 (3H,s), 4.01 (4H,bs), 4.22 (2H, m), 4.43 (2H,m), 6.41 (2H,bs), 6.52 (2H,bs), 8.01 (1H,s), 8.11 (1H,s), 8.45 (6H,bs) IR (KBr) $cm^{-1}$ 3291, 2130, 1702, 1645, 1599, 1582, 1548, 1486, 1102

Compound 34-3

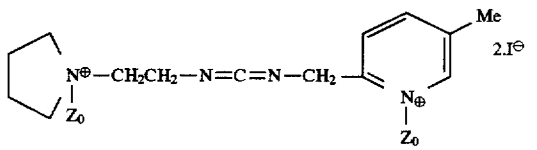

$^1$H-NMR (DMSO-$d_6$) δ=1.21–2.32 (32H,m), 2.61–3.64 (26H,m), 2.61 (3H,s), 4.26 (2H,m), 4.42 (2H,m), 4.72 (2H, s), 6.41 (2H,m), 6.50 (2H,m), 8.01 (1H,d), 8.41 (2H,bs), 8.51 (1H,d), 8.92 (1H,s) IR (KBr) $cm^{-1}$ 3292, 2130, 1703, 1644, 1598, 1581, 1549, 1484

Compound 34-4

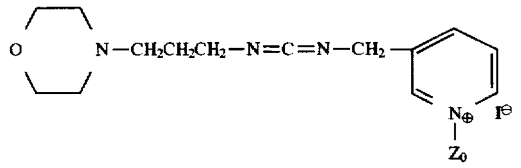

$^1$H-NMR (DMSO-$d_6$) δ=1.10–1.75 (14H,m), 1.85–1.95 (2H,m), 2.05 (2H,t), 2.41 (4H,bs), 2.55 (1H,d), 2.80 (1H,dd), 2.95–3.10 (3H,m), 3.20–3.50 (4H,m), 3.60 (4H,bs), 4.15 (1H,m), 4.30 (1H,m), 4.60 (2H,t), 4.75 (2H,s), 6.35 (1H,s), 6.45 (1H,s), 7.70–7.80 (1H,m), 8.15 (1H,t), 8.55 (1H,d), 9.05 (1H,d), 9.10 (1H,s) IR (KBr) $cm^{-1}$ 3290, 2930, 2130, 1700, 1660, 1540, 1460

Compound 35-1

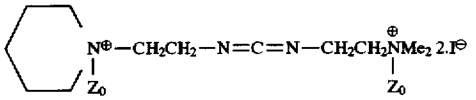

$^1$H-NMR (DMSO-$d_6$) δ=1.21–2.33 (34H,m), 2.61–3.62 (30H,m), 3.51 (6H,s), 4.24 (2H,m), 4.42 (2H,m), 6.41 (2H, bs), 6.52 (2H,bs), 8.45 (2H,bs) IR (KBr) $cm^{-1}$ 3291, 2130, 1702, 1645, 1549

Compound 35-2

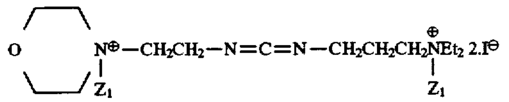

$^1$H-NMR (DMSO-$d_6$) δ=1.21–2.32 (44H,m), 2.61–3.67 (50H,m), 4.01 (4H,bs), 4.24 (2H,m), 4.45 (2H,m), 6.41 (2H,bs), 6.51 (2H,bs), 8.44 (6H,bs) IR (KBr) $cm^{-1}$ 3292, 2131, 1703, 1644, 1548, 1102

Compound 35-3

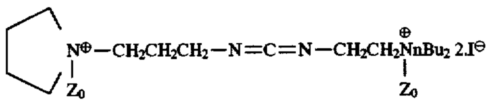

$^1$H-NMR (DMSO-$d_6$) δ=0.92 (6H,t), 1.21–2.32 (42H,m), 2.62–3.64 (34H,m), 4.22 (2H,m), 4.44 (2H,m), 6.40 (2H,bs), 6.50 (2H,bs), 8.45 (2H,bs) IR (KBr) $cm^{-1}$ 3291, 2130, 1702, 1644, 1548

Compound 35-4

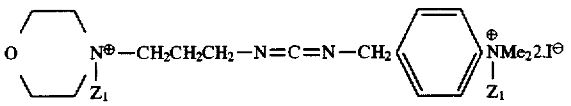

$^1$H-NMR (DMSO-$d_6$) δ=1.21–2.32 (38H,m), 2.61–3.63 (42H,m), 4.02 (4H,bs), 4.24 (2H ,m), 4.42 (2H,m), 4.72 (2H,s), 4.92 (6H,s), 6.40 (2H,bs), 6.50 (2H,bs), 7.62 (2H,d), 7.81 (2H,d), 8.45 (6H,bs) IR (KBr) $cm^{-1}$ 3288, 2129, 1704, 1645, 1549, 1110

Compound 36-1

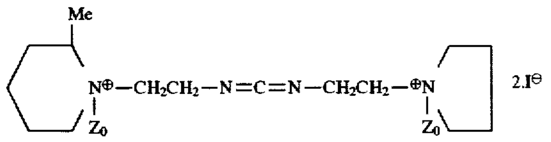

$^1$H-NMR (DMSO-$d_6$) δ=1.10 (3H,d), 1.21–1.72 (26H,m), 2.01 (4H,t), 2.12 (2H,m), 2.53 (4H,d), 2.86 (4H,dd), 3.05–3.74 (20H,m), 4.07 (1H,m), 4.12 (2H,m), 4.36 (2H,m), 6.39 (2H,bs), 6.45 (2H,bs), 7.78 (2H,bs) IR (KBr) $cm^{-1}$ 3288, 2126, 1704, 1643, 1550

Compound 36-2

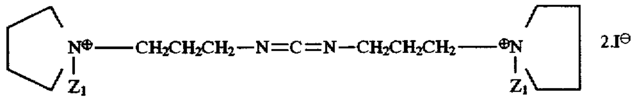

$^1$H-NMR (DMSO-$d_6$) δ=1.22–1.74 (22H,m), 2.03–2.12 (24H,m), 2.66 (4H,d), 2.85 (4H,dd), 2.92–3.72 (26H,m), 4.11 (2H,m), 4.33 (2H,m), 6.36 (2H,bs), 6.44 (2H,bs), 7.87 (6H,bs) IR (KBr) $cm^{-1}$ 3290, 2123, 1703, 1642, 1548

Compound 36-3

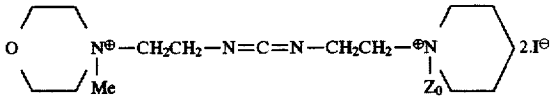

$^1$H-NMR (DMSO-$d_6$) δ=1.32–1.95 (26H,m), 2.00 (2H,t), 2.54 (4H,d), 2.87 (4H,dd), 3.02–3.78 (22H,m), 4.03 (4H,d), 4.16 (2H,m), 4.33 (2H,m), 6.36 (2H,bs), 6.45 (2H,bs), 7.78 (2H,bs) IR (KBr) $cm^{-1}$ 3287, 2124, 1705, 1648, 1552

Compound 36-4

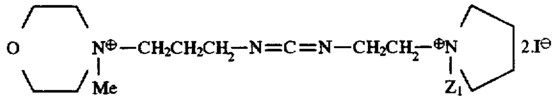

$^1$H-NMR (DMSO-$d_6$) δ=1.21–1.74 (44H,m), 2.05–2.12 (18H,m), 2.63 (4H,m), 2.87 (4H,dd), 2.92–3.74 (26H,m), 4.01 (4H,d), 4.13 (2H,m), 4.33 (2H,m), 6.36 (2H,bs), 6.45 (2H,bs), 7.80 (6H,bs) IR (KBr) $cm^{-1}$ 3286, 2125, 1706, 1650, 1550

Compound 37-1

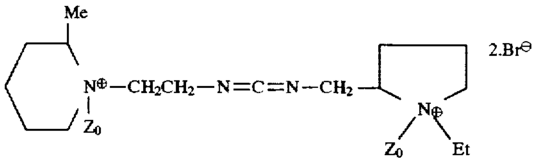

$^1$H-NMR (DMSO-$d_6$) =1.11–1.74 (32H,m), 2.06–2.14 (8H, m), 2.55 (4H,d), 2.83 (4H,dd), 3.01–3.98 (17H,m), 4.15 (2H,m), 4.38 (2H,m), 6.39 (2H,bs), 6.47 (2H,bs), 7.77 (2H,bs) IR (KBr) $cm^{-1}$ 3290, 2125, 1705, 1650, 1549

Compound 37-2

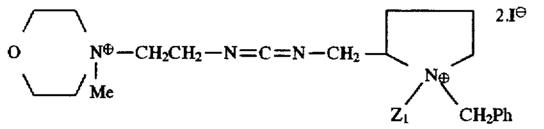

$^1$H-NMR (DMSO-$d_6$) δ=1.22–1.73 (44H,m), 2.04–2.11 (14H,m), 2.64 (4H,d), 2.79 (4H,dd), 2.92–3.38 (15H,m), 3.48–4.01 (14H,m), 4.13 (2H,m), 4.33 (2H,m), 6.35 (2H,bs), 6.43 (2H,bs), 6.62 (2H,q), 7.18 (2H,dd), 7.79 (6H,bs), 7.94 (1H,dd) IR (KBr) $cm^{-1}$ 3287, 2123, 1703, 1648, 1548, 1490, 1110

Compound 37-3

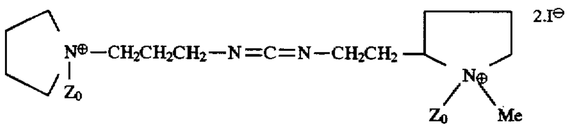

$^1$H-NMR (DMSO-$d_6$) δ=1.24–1.69 (44H,m), 2.02–2.14 (24H,m), 2.59 (4H,d), 2.82 (4H,dd), 2.87–3.51 (13H,m), 3.56–3.87 (13H,m), 4.11 (2H,m), 4.26 (2H,m), 6.33 (2H,bs), 6.39 (2H,bs), 7.74 (2H,bs) IR (KBr) $cm^{-}$3288, 2128, 1704, 1647, 1550

Compound 38-1

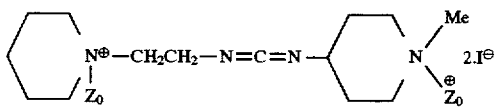

$^1$H-NMR (DMSO-$d_6$) δ=1.28–2.02 (31H,m), 2.52 (4H,d), 2.77 (4H,dd), 3.02–3.14 (6H,m), 3.59–3.68 (13H,m), 4.11 (2H,m), 4.26 (2H,m), 6.33 (2H,bs), 6.42 (2H,bs), 7.71 (2H,bs) IR (KBr) $cm^{-1}$ 3290, 2126, 1700, 1650, 1552

Compound 38-2

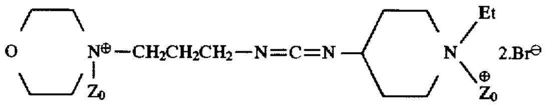

$^1$H-NMR (DMSO-$d_6$) δ=1.29–2.02 (28H,m), 2.51 (4H,d), 2.78 (4H,dd), 3.02–3.11 (6H,m), 3.46–4.01 (14H,m), 4.13 (2H,m), 4.29 (2H,m), 6.30 (2H,bs), 6.41 (2H,bs), 7.71 (2H,bs) IR (KBr) $cm^{-1}$ 3288, 2124, 1703, 1647, 1547, 1105

Compound 38-3

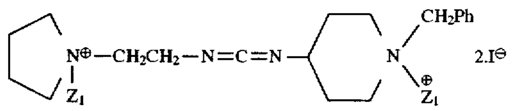

$^1$H-NMR (DMSO-$d_6$) δ=1.19–1.72 (48H,m), 2.02–2.11 (17H,m), 2.89–3.68 (24H,m), 4.12 (2H,m), 4.33 (2H,m), 6.29 (2H,bs), 6.41 (2H,bs), 7.01–7.51 (5H,m), 7.79 (6H,bs) IR (KBr) $cm^{-1}$ 3290, 2126, 1702, 1644, 1548, 1488

Compound 39-1

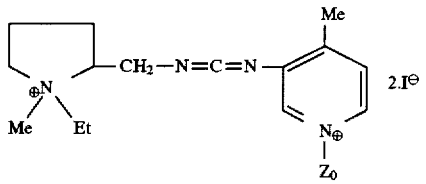

$^1$H-NMR (DMSO-$d_6$) δ=1.29–1.72 (13H,m), 2.01–2.11 (6H, m), 2.48–2.82 (7H,m), 3.01–3.29 (8H,m), 3.57–3.89 (5H, m), 4.08 (1H,m), 4.26 (1H,m), 6.32 (1H,bs), 6.41 (1H,bs), 7.74 (1H,bs), 8.32 (1H,d), 9.00 (1H,d), 9.09 (1H,s) IR (KBr) $cm^{-1}$ 3288, 2150, 1703, 1648, 1576, 1549, 1424

Compound 39-2

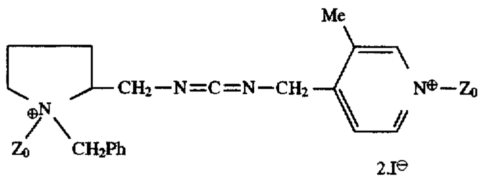

$^1$H-NMR (DMSO-$d_6$) δ=1.28–1.69 (20H,m), 2.01–2.11 (8H, m), 2.47 (7H,m), 2.82 (4H,dd), 3.01–3.34 (9H,m), 3.91 (4H,m), 4.06 (2H,m), 4.25 (2H,m), 6.31 (2H,bs), 6.42 (2H, d), 7.01–7.49 (5H,m), 7.69 (2H,bs), 8.58 (1H,d), 9.03 (1H, d), 9.46 (1H,s) IR (KBr) $cm^{-1}$ 3289, 2148, 1700, 1643, 1595, 1549, 1488, 1423

Compound 39-3

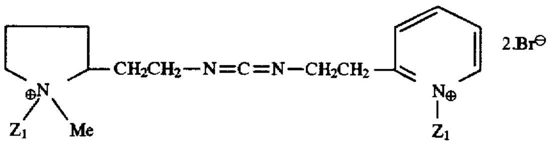

$^1$H-NMR (DMSO-$d_6$) δ=1.19–1.72 (44H,m), 2.02–2.13 (18H,m), 2.60 (4H,d), 2.76 (4H,dd), 3.26–3.42 (3H,m), 2.91–3.62 (15H,m), 4.06–4.28 (6H,m), 6.32 (2H,bs), 6.42 (2H,bs), 7.79 (6H,bs), 8.22 (1H,q), 8.45 (1H,q), 9.02 (1H, dd), 9.11 (1H,dd) IR (KBr) $cm^{-1}$ 3280, 2132, 1704, 1648, 1560, 1548, 1424

Compound 40-1

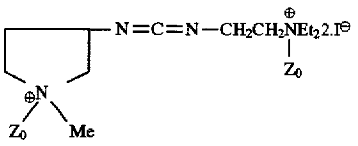

$^1$H-NMR (DMSO-$d_6$) δ=1.29–1.72 (23H,m), 2.01–2.63 (11H,m), 2.78 (4H,dd), 2.99–3.12 (6H,m), 3.46–3.63 (13H, m), 4.11 (2H,m), 4.32 (2H,m), 6.42 (2H,bs), 7.73 (2H,bs) IR (KBr) $cm^{-1}$ 3288, 2126, 1703, 1645, 1549

Compound 40-2

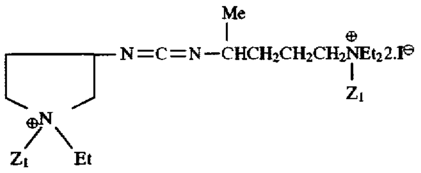

$^1$H-NMR (DMSO-$d_6$) δ=1.19–1.74 (51H,m), 2.00–2.62 (23H,m), 2.82 (4H,dd), 2.91–3.56 (21H,m), 4.11 (2H,m), 4.26 (2H,m), 6.32 (2H,bs), 6.42 (2H,bs), 7.81 (6H,bs) IR (KBr) $cm^{-1}$ 3284, 2122, 1704, 1648, 1545

Compound 40-3

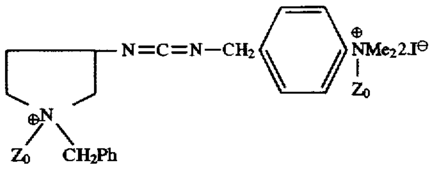

$^1$H-NMR (DMSO-$d_6$) δ=1.31–1.72 (20H,m), 1.98–2.79 (15H,m), 3.02–3.11 (4H,m), 3.62–3.91 (12H,m), 4.13 (2H, m), 4.33 (2H,m), 4.63 (2H,d), 6.34 (2H,bs), 6.41 (2H,bs), 7.00–7.53 (5H,m), 7.74 (2H,bs) IR (KBr) $cm^{-1}$ 3283, 2214, 1704, 1645, 1605, 1558, 1547, 1424

Compound 40-4

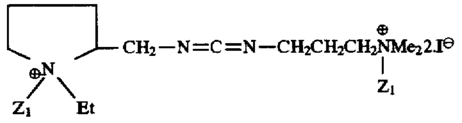

$^1$H-NMR (DMSO-$d_6$) δ=1.22–1.71 (47H,m), 2.03–2.84 (25H,m), 2.91–3.62 (28H,m), 4.11 (2H,m), 4.33 (2H,m), 6.32 (2H,bs), 6.41 (2H,bs), 7.79 (6H,bs) IR (KBr) $cm^{-1}$ 3282, 2123, 1702, 1644, 1548

Compound 41-1

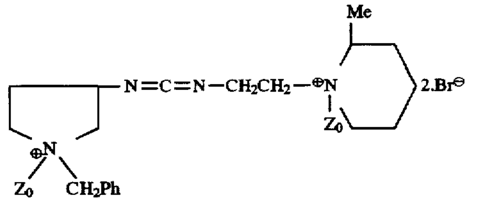

$^1$H-NMR (DMSO-$d_6$) δ=1.18–1.69 (29H,m), 2.02–2.78 (15H,m), 3.01–3.74 (18H,m), 4.03–4.29 (5H,m), 6.33 (2H, bs), 6.41 (2H,bs), 7.01–7.48 (5H,m), 7.74 (2H,bs) IR (KBr) $cm^{-1}$ 3285, 2124, 1701, 1648, 1560, 1549, 1420

Compound 41-2

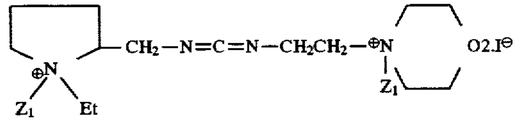

$^1$H-NMR (DMSO-$d_6$) δ=1.19–1.70 (47H,m), 2.01–2.12 (16H,m), 2.56 (4H,d), 2.82 (4H,dd), 2.93–3.89 (25H,m), 4.01–4.09 (6H,m), 4.29 (2H,m), 6.33 (2H,bs), 6.41 (2H,bs), 7.78 (6H,bs) IR (KBr) $cm^{31}$ 13283, 2120, 1702, 1644, 1552, 1117

Compound 41-3

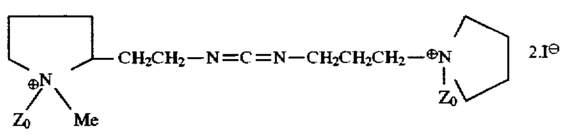

$^1$H-NMR (DMSO-$d_6$) δ=1.32–1.69 (20H,m), 2.01–2.12 (14H,m), 2.49 (4H,d), 2.79 (4H,dd9, 3.01–3.94 (23H,m), 4.06 (2H,m), 4.32 (2H,m), 6.32 (2H,bs), 6.41 (2H,bs), 7.69 (2H,bs) IR (KBr) $cm^{-1}$ 3287, 2120, 1704, 1645, 1548

Compound 42-1

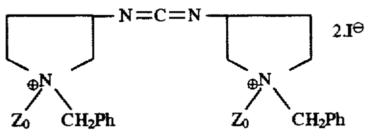

$^1$H-NMR (DMSO-$d_6$) δ=1.28–1.71 (10H,m), 2.01–2.56 (14H,m), 2.82 (4H,dd), 3.01–3.56 (18H,m), 4.09 (2H,m), 4.28 (2H,m), 6.29 (2H,bs), 6.41 (2H,bs)7.02–7.45 (10H,m), 7.71 (2H,bs) IR (KBr) $cm^{-1}$ 3284, 2128, 1702, 1648, 1565, 1547, 1421

Compound 42-2

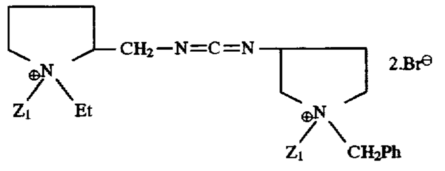

$^1$H-NMR (DMSO-$d_6$) δ=1.22–1.69 (47H,m), 2.00–2.29 (18H,m), 2.62 (5H,m), 2.81 (4H,dd), 2.91–3.89 (23H,m), 4.05 (2H,m), 4.29 (2H,m), 6.32 (2H,bs), 6.42 (2H,bs), 7.01–7.46 (5H,m), 7.78 (6H,bs) IR (KBr) $cm^{-1}$ 3289, 2124, 1703, 1649, 1560, 1549, 1419

Compound 42-3

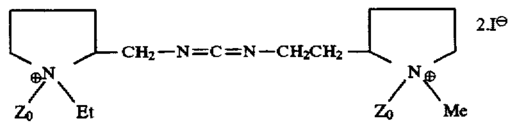

$^1$H-NMR (DMSO-$d_6$) δ=1.32–1.74 (23H,m), 2.02–2.59 (9H,m), 2.82 (4H,dd), 3.01–3.32 (8H,m), 3.59–3.91 (11H, m), 4.09 (2H,m), 4.32 (2H,m), 6.33 (2H,bs), 6.39 (2H,bs), 7.70 (2H,bs) IR (KBr) $cm^{-1}$ 3287, 2122, 1705, 1648, 1546

Compound 43-1

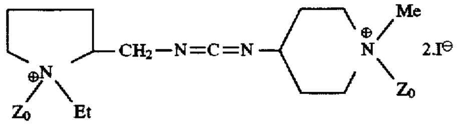

$^1$H-NMR (DMSO-$d_6$) δ=1.26–1.69 (27H,m), 2.01–2.09 (9H,m), 2.52 (4H,d), 2.82 (4H,dd), 3.01–3.13 (6H,m), 3.33–3.64 (14H,m), 4.06 (2H,m), 4.26 (2H,m), 6.34 (2H,bs), 6.39 (2H,bs), 7.71 (2H,bs) IR (KBr) $cm^{-1}$ 3287, 2121, 1702, 1650, 1547

Compound 43-2

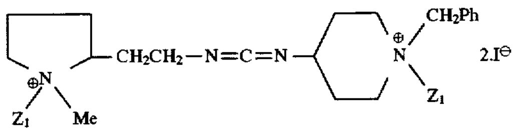

$^{1}$H-NMR (DMSO-$d_6$) δ=1.21–1.69 (48H,m), 2.01–2.13 (19H,m), 2.56 (4H,d), 2.79 (4H,dd), 2.91–3.56 (24H,m), 4.06 (2H,m), 4.32 (2H,m), 6.33 (2H,bs), 6.41 (2H,bs), 7.00–7.45 (5H,m), 7.78 (2H,bs) IR (KBr) $cm^{-1}$ 3284, 2125, 1701, 1647, 1557, 1548, 1422

Compound 44-1

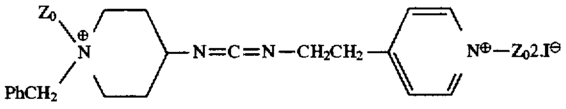

$^{1}$H-NMR (DMSO-$d_6$) δ=1.25–1.65 (24H,m), 1.99–2.12 (5H,m), 2.53 (4H,d), 2.78 (4H,dd), 2.97–3.15 (8H,m), 3.62–3.69 (6H,m), 4.06–4.28 (6H,m), 6.32 (2H,bs), 6.41 (2H,bs), 7.01–7.46 (5H,m), 7.74 (2H,bs), 8.59 (2H,d), 9.10 (2H,d) IR (KBr) $cm^{-1}$ 3281, 2219, 1708, 1646, 1575, 1559, 1547, 1428, 1419

Compound 45-1

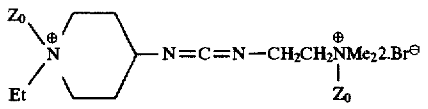

$^{1}$H-NMR (DMSO-$d_6$) δ=1.25–1.69 (27H,m), 1.98–2.10 (5H,m), 2.45 (4H,d), 2.78 (4H,dd), 3.01–3.14 (6H,m), 3.45–3.56 (16H,m), 4.12 (2H,bs), 4.32 (2H,bs), 6.30 (2H, bs), 6.41 (2H,bs), 7.74 (2H,bs) IR (KBr) $cm^{-1}$ 3286, 2124, 1704, 1644, 1548

Compound 45-2

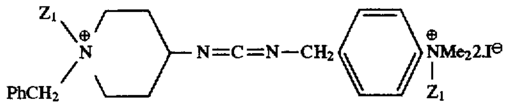

$^{1}$H-NMR (DMSO-$d_6$) δ=1.21–1.69 (48H,m), 2.03–2.11 (13H,m), 2.58 (4H,d), 2.82 (4H,dd), 2.90–3.65 (22H,m), 4.05 (2H,m), 4.32 (4H,m), 6.32 (2H,bs), 6.44 (2H,bs), 7.52 (4H,d), 7.84 (6H,bs), 8.02 (4H,d) IR (KBr) $cm^{-1}$ 3283, 2211, 1702, 1645, 1561, 1558, 1548, 1421

Compound 46-1

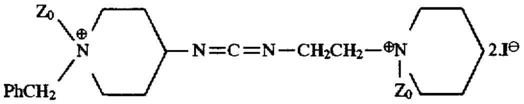

$^{1}$H-NMR (DMSO-$d_6$) δ=1.32–1.74 (28H,m), 2.01–2.11 (6H, m), 2.45 (4H,d), 2.78 (4H,dd), 3.01–3.12 (6H,m), 3.61–3.70 (14H,m), 4.11 (2H,m), 4.33 (2H,m), 6.25 (2H,bs), 6.41 (2H,bs), 7.02–7.46 (5H,m), 7.69 (2H,bs) IR (KBr) $cm^{-1}$ 3285, 2124, 1702, 1643, 1561, 1548

Compound 46-2

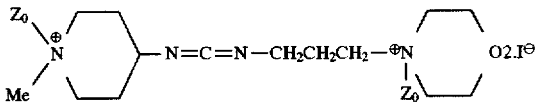

1H-NMR (DMSO-$d_6$) δ=1.25–1.66 (27H,m), 2.03–2.09 (7H,m), 3.04–3.12 (6H,m), 3.45–4.03 (19H,m), 4.05 (2H, m), 4.32 (2H,m), 6.33 (2H,m), 6.41 (2H,bs), 7.69 (2H,bs) IR (KBr) $cm^{-1}$ 3283, 2125, 1703, 1641, 1548, 1116

Compound 46-3

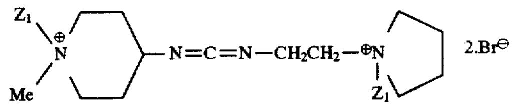

$^{1}$H-NMR (DMSO-$d_6$) δ=1.25–1.66 (48H,m), 1.99–2.08 (17H,m), 2.56 (4H,d), 2.82 (4H,dd), 2.89–3.65 (22H,m), 4.19 (2H,m), 4.31 (2H,m), 6.32 (2H,bs), 6.41 (2H,bs), 7.78 (6H,bs) IR (KBr) $cm^{-1}$ 3290, 2129, 1705, 1643, 1550

Compound 47-1

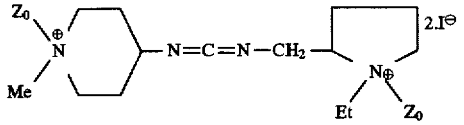

$^{1}$H-NMR (DMSO-$d_6$) δ=1.26–1.68 (24H,m), 2.01–2.13 (9H,m), 2.45 (4H,d), 2.78 (4H,dd), 3.01–3.14 (6H,m), 3.32–3.85 (12H,m), 4.14 (2H,m), 4.32 (2H,m), 6.32 (2H,bs), 6.39 (2H,bs), 7.71 (2H,bs) IR (KBr) $cm^{-1}$ 3286, 2127, 1701, 1641, 1547

Compound 47-2

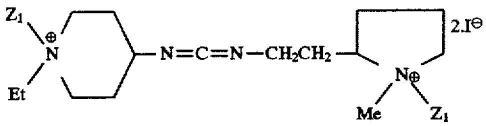

$^{1}$H-NMR (DMSO-$d_6$) δ=1.26–1.71 (51H,m), 2.01–2.12 (19H,m), 2.56 (4H,d), 2.78 (4H,dd), 2.89–3.56 (21H,m), 4.05 (2H,m), 4.29 (2H,m), 6.32 (2H,bs), 6.41 (2H,bs), 7.76 (6H,bs) IR (KBr) $cm^{-1}$ 3289, 2124, 1699, 1640, 1548

Compound 48-1

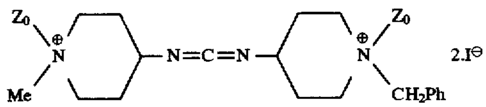

$^{1}$H-NMR (DMSO-$d_6$) δ=1.31–1.74 (52H,m), 2.03–2.11 (14H,m), 2.58 (4H,d), 2.81 (4H,dd), 2.89–3.55 (23H,m), 4.05 (2H,m), 4.29 (2H,m), 6.32 (2H,bs), 6.41 (2H,bs), 7.02–7.48 (5H,m), 7.69 (2H,bs) IR (KBr) $cm^{-1}$ 3287, 2128, 1705, 1644, 1561, 1547

Use of Compounds

Use Example 1

Biotin Labelling of DNA

A reaction system [1 μg of M13mp18RF DNA (a product of Takara Shuzo Co., Ltd.), 0.1M borate buffer (pH 8.5), 0.25% SDS, 0.1M compound 30-1] was incubated at 85° C.

for 1 minute to conduct biotin labelling of DNA. To remove unreacted carbobiotin, 3M sodium acetate of 1/9 time the volume of the sample and cold ethanol of 2.5 times the volume of the sample were added, followed by mixing. The resulting mixture was allowed to stand at −80° C. for 45 minutes. Centrifugation was conducted using a centrifuge (H-1500 FR made in Japan), at 12,000 rpm at 4° C. for 15 minutes. The upper layer was removed; 500 μl of 70% ethanol was added; and centrifugation was conducted at 12,000 rpm at 4° C. for 1 minute and 30 seconds. The upper layer was removed; the residue was dissolved in 100 μl of sterilized water; and the solution was stored at −20° C.

Use Example 2

Dot Blotting Detection

The biotin-labelled DNA obtained in Use Example 1 was subjected to dot blotting detection in the following manner.

(Immobilization of DNA)

The DNA concentration in the biotin-labelled DNA solution was examined using an UV tester (UV-VISIBLE RECORDING SPECTROPHOTOMETER UV-2100, a product of Shimadzu Corporation). Then, dilutions of the biotin-labelled DNA were prepared and each 1 μl of the dilutions was dot-blotted on a nylon membrane (Hybond $N^+$, a product of Amersham K.K.). The membrane was dried, after which UV-crosslinking was conducted using UV Stratalinker® (a product of STRATAGENE) to immobilize the DNA on the membrane.

(Chemical color development)

The membrane was placed in a hybridization bag (BRL: Bethesda Research Laboratories), then immersed in 5 ml, per 100 $cm^2$ of the membrane, of a buffer B solution [3% BSA, 0.2M NaCl, 0.1M Tris-HCl (pH 7.5), 0.05% Triton-X-100], and allowed to stand at room temperature for 30 minutes. Thereafter, the membrane was immersed in a solution obtained by adding 2.5 μl of Streptavidin-alkaline phosphatase conjugate (CLONTECH) to 1 ml, per 100 $cm^2$ of the membrane, of a buffer A solution [0.2M NaCl, 0.1M Tris-HCl (pH 7.5), 0.05% Triton-X-100], and then allowed to stand at room temperature for 25 minutes. The membrane was washed with 100 ml of a buffer A solution for 10 minutes, and this washing was conducted two more times (three times in total). The membrane in the hybridization bag was immersed in 5 ml, per 100 $cm^2$ of the membrane, of a solution obtained by adding 32 μl of NBT (nitroblue tetrazolium salt) and 16 μl of X-phosphate to 5 ml of a buffer C solution [0.1M NaCl, 0.1M Tris-HCl (pH 9.5), 50 m mol $MgCl_2$], and color development was conducted in a dark place for 30 minutes. The membrane was washed thoroughly with sterilized water, dried and stored. The DNA labelled with compound 30-1 could be detected to as low as 0.01 pg. The DNA labelled with Photobiotin, when subjected to the same color development, could be detected to as low as 1 pg.

Use Example 3

Dot Hybridization

Dot hybridization was conducted as follows using, as a probe, (1) a DNA labelled with compound 15-1 in the same manner as in Use Example 1 except that the reaction temperature and time was 40° C. and 5 minutes and (2) a DNA labelled with Photobiotin.

(Immobilization of DNA)

Dilutions of unlabelled M13mp18RF DNA (a product of Takara Shuzo Co., Ltd.) were prepared. Each 2 μl of the dilutions was incubated at 100° C. for 10 minutes, and then allowed to stand in ice for 5 minutes. To each of the resulting dilutions was added 2 μl of a 0.4N aqueous sodium hydroxide solution, followed by mixing to give rise to alkali denaturation of DNA at room temperature for 20 minutes. Neutralization with 1.5 μl of 3M sodium acetate was conducted, and the reaction mixture was transferred into ice. Thereto was added 4.5 μl of sterilized water, followed by mixing. Each 1 μl of the mixtures was dot-blotted on a nylon membrane, then dried, and UV-crosslinked to immobilize the denatured DNA on the membrane.

(Hybridization)

The membrane in a hybridization bag was immersed in 5 ml, per 100 $cm^2$ of the membrane, of a prehybridization solution [four-fold diluted SSC solution (see *1 for SSC solution), ten-fold diluted Denhardt's solution (see *2 for Denhardt's solution), 25 m mol sodium phosphate (pH 6.5), 50% formamide, 0.5 mg/ml freshly denatured salmon sperm DNA], to conduct incubation at 42° C. for 2 hours. Then, the membrane was immersed in 1 ml, per 100 $cm^2$ of the membrane, of a hybridization solution [four-fold diluted SSC solution, Denhardt's solution, 25 m mol sodium phosphate (pH 6.5), 45% formamide, 0.2 mg/ml freshly denatured salmon sperm DNA, 20 ng/ml DNA probe labelled with compound 15-1 or with Photobiotin], followed by incubation at 42° C. overnight.

(Post-hybridization Washing)

The resulting membrane was immersed in 100 ml of a ten-fold diluted SSC solution containing 0.1% of SDS, and shaken at room temperature for 5 minutes. This washing operation was conducted twice. Then, a washing operation using 100 ml of a 100-fold diluted SSC solution containing 0.1% of SDS was conducted twice. Thereafter, incubation at 50° C. for 15 minutes in 50 ml of a 125-fold diluted SSC solution containing 0.1% of SDS was conducted twice. The resulting membrane was washed with 25 ml of a 20-fold diluted SSC solution and subjected to the following chemical color development.

(Chemical Color Development)

Chemical color development was conducted in the same manner as in Use Example 2 except that the volume of Strepavidin-alkaline phosphatase conjugate used was reduced to 1/3 and the time of color development was 5 hours. When the Photobiotin-labelled DNA probe was used, the template DNA could be detected to as low as 10 pg. When the DNA probe labelled with compound 15-1 was used, the template DNA could be detected to as low as 0.1 pg.

Use Example 4

Southern Hybridization

Southern hybridization was conducted as follows using, as a probe, a DNA labelled with compound 43-2 in the same manner as in Use Example 1 except that the reaction temperature and time was 30° C. and 10 minutes.

Each 10 μl of dilutions of λ/Hind III digest DNAs (DNA ?) (a product of Takara Shuzo Co., Ltd.) was prepared. To each dilution was added 1 μl of a gel-loading solution [30% glycerol, 0.25% Bromophenol Blue (BPB), 0.25% xylene cyanol (XC)]. The mixture was subjected to 1% agarose electrophoresis [T. Maniatis et al., Molecular Cloning, second edition, p. 6 (1989), Cold Spring Harbor], and migration was conducted at 100 V for 2 hours. Then, the gel end was cut off and immersed in a denaturing solution [0.2N NaOH, 0.6M NaCl]. The mixture was shaken for 30 minutes. Then, the gel was washed with deionized water and immersed in a neutralizing solution [0.24M Tris-HCl (pH 7.5), 0.6M NaCl] for 30 minutes twice. The DNA in the resulting gel was transferred on a nylon membrane immersed in deionized water and a two-fold diluted SSC solution, by the use of a two-fold diluted SSC solution in one night. The DNA-transferred membrane was dried and UV crosslinking was conducted to immobilize the DNA on the membrane. Then, hybridization and chemical color development were conducted in the same manner as in Use Example 3. Detection was possible to as low as 0.5 pg. When the same operation was conducted using the Photobiotin-labelled DNA, detection was possible to as low as 5 pg.

*1: SSC solution
3M NaCl
0.3M sodium citrate, pH 7.0

*2: Denhardt's solution
1% Ficol
1% Polyvinylpyrrolidone
1% BSA, Fraction V.

Use Example 5

Hybridization Using Microtiter Plate (Denaturation of Immobilized ? Nucleic Acid)

M13mp18RF, which had been made into a straight chain by the use of a restriction enzyme (Hind III), was dissolved in 2M NaCl in various concentrations to prepare six dilutions containing the M13mp18RF in concentrations of 48 ng/100 μl to 480 fg/100 μl (the concentration of a dilution over that of the next lower concentration dilution was 10-fold). Each dilution was heat-treated at 100° C. for 10 minutes and quenched in ice for 5 minutes.

(Immobilization of Denatured Nucleic Acid on Plate)

The dilutions after heat treatment each containing a heat-denatured nucleic acid were placed in the wells of an immunomodule microtiter plate (a product of NIPPON INTERNED K.K.), and the plate was sealed. Immobilization was conducted at 37° C. for 12 hours.

(Prehybridization)

The plate having denatured M13RF immobilized thereon was washed with distilled water. In each well of the plate was placed 100 μl of a prehybridization solution. Then, the plate was sealed and incubation was conducted at 60° C. for 1.5 hours.

Incidentally, the prehybridization solution had the following composition.

A four-fold diluted SSC solution, a ten-fold diluted Denhardt's solution, a 25 m mol sodium phosphate buffer solution (pH 6.5), 50% formamide, 0.5 mg/ml transfer RNA of yeast (Hybridization)

The prehybrdization solution in each well of the plate was discarded, and 100 μl of a hybridization solution was placed in each well. Incubation was conducted at 42° C. for 12 hours.

Incidentally, the hybridization solution had the following composition.

A four-fold diluted SSC solution, a Denhardt's solution, a 25 m mol sodium phosphate buffer solution (pH 6.5), 45% formamide, 0.2 mg/ml transfer RNA of yeast, 640 ng/ml biotin-introduced M13 single-stranded DNA The biotin-introduced M13 single-stranded DNA was obtained by introducing biotin (compound 24-1) in the same manner as in Use Example 1. The biotin-introduced DNA was heat-treated at 75° C. for 10 minutes, quenched in ice for 5 minutes and then added to a mixture of the components of the hybridization solution other than the biotin-introduced DNA.

(Removal of Unreacted Biotin-introduced Nucleic Acid)

The biotin-introduced single-stranded M13 DNA, which did not form a hybrid with the immobilized heat-denatured M13RF, was removed by the following procedure.

The hybridization solution in each well was removed. In each well was placed 150 μl of an aqueous ten-fold diluted SSC solution containing 0.1% of sodium dodecyl sulfate. The plate was shaken by the use of a plate mixer at room temperature for 5 minutes. This operation was conducted two more times. The solution in each well was discarded. In each well was placed 150 μl of an aqueous 100-fold diluted SSC solution containing 0.1% sodium dodecyl sulfate. The plate was shaken at 42° C. for 5 minutes. This operation was conducted two more times. The solution in each well was discarded. 300 μl of a 10-fold diluted SSC solution was added, after which the plate was allowed to stand at room temperature for 5 minutes.

(Detection of Hybrid Nucleic Acid)

The solution in each well was discarded. In each well was placed 300 μl of Buffer B (the composition was the same as that used in Use Example 1 (2?)), after which the plate was allowed to stand at room temperature for 30 minutes. The solution in each well was discarded. In each well was placed 100 μl of strepavidin-alkaline phosphatase, and incubation was conducted for 25 minutes. The solution in each well was discarded. In each well was placed 200 μl of Buffer A (the composition was the same as that used in Use Example 1 (2?)), and the plate was shaken at room temperature for 5 minutes. This operation was conducted two more times. The solution in each well was discarded. In each well was placed 100 μl of a pNpp solution, and the plate was sealed. A reaction was conducted at 30C for 30 minutes. Absorption at 405 nm was measured using a microplate reader (MTP-120, a product of Corona Denki K.K.). As a result, M13RF of 4.8 pg could be detected. The composition of the pNpp solution is shown below.

50 m mol of sodium tetraborate (pH 10.0), 5 m mol magnesium chloride, 5 m mol sodium p-nitrophenylphosphate Use Example 6

Hybridization using Biotin-introduced DNA

The following test was conducted using an oligomer DNA (30 mer) containing a sequence complementary to M13 DNA, which had been labelled with compound 29-1 in the same operation as used in Use Example 1 except that the reaction temperature and time were 20° C. and 5 minutes. In the same manner as in Use Example 3, M13RF, EDNA was denatured, immobilized on a nylon membrane, and subjected to hybridization with a biotin-introduced oligomer probe. Then, washing was conducted and chemical color development was conducted for detection in the same manner as in Use Example 2. Signals were detected only at the sites where M13RF had been immobilized.

What is claimed is:

1. A carbodiimide derivative represented by the following general formula (I)

$$W_1—X—N=C=N—Y—W_2—Z \quad (I)$$

wherein $W_1$ is a straight chain, branched chain or cyclic saturated or unsaturated aliphatic hydrocarbon group, a substituted or unsubstituted aryl group, a heteroaryl group, a tertiary amino group or a tertiary or quaternary ammonium group; —$W_2$—Z is a quaternary ammonium group; X and Y are each independently a single bond or an alkylene group whose main chain has 1–20 carbon atoms and which may have at least one branch having 24 or less carbon atoms; and Z is a biotin group represented by the following formula (a):

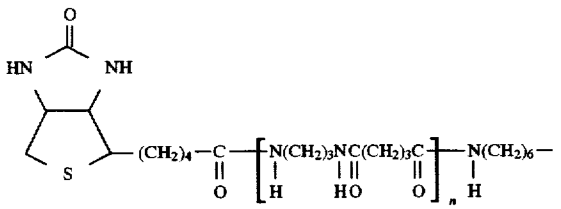
(a)

wherein n is 0 or 1;

excluding the compounds wherein $W_1$ is a tertiary amino group or a tertiary or quaternary ammonium group represented by the following formula:

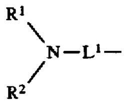
(b)

or

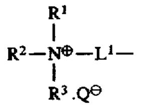
(c)

wherein $R^1$ and $R^2$ are each independently a straight chain, branched chain or cyclic saturated or unsaturated $C_1$–$C_{10}$ aliphatic hydrocarbon group or a substituted or unsubstituted aryl or aralkyl group; $R^3$ is a hydrogen atom, a straight chain, branched chain or cyclic saturated or unsaturated $C_1$–$C_{10}$ aliphatic hydrocarbon group, a substituted or unsubstituted aryl or aralkyl group, or a biotin group of the formula (a) as defined above; $L^1$ is a single bond or an o-, m- or p-phenylene group which may be substituted with at least one $C_1$–$C_{10}$ alkyl group; $Q^-$ is a counter anion; —$W_2$—Z is a quaternary ammonium group represented by the following formula (g):

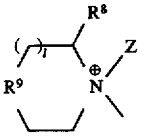
(g)

wherein $R^8$ is a hydrogen atom or $R^6$; $R^6$ is a straight chain, branched chain or cyclic saturated or unsaturated $C_1$–$C_{10}$ aliphatic hydrocarbon group or a substituted or unsubstituted aryl or aralkyl group; Z is a biotin group of the formula (a) as defined above; $R^9$ is an oxygen atom or a methylene group; and l is 0 or 1.

2. A compound according to claim 1, wherein $W_1$ is a tertiary amino group or a tertiary or quaternary ammonium group, represented by the following formula:

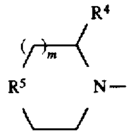
(d)

or

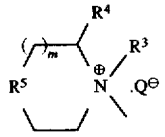
(e)

wherein $R^4$ is a hydrogen atom or $R^1$; $R^1$ is a straight chain, branched chain or cyclic saturated or unsaturated $C_1$–$C_{10}$ aliphatic hydrocarbon group or a substituted or unsubstituted aryl or aralkyl group; $R^3$ is a hydrogen atom, a straight chain, branched chain or cyclic saturated or unsaturated $C_1$–$C_{10}$ aliphatic hydrocarbon group, a substituted or unsubstituted aryl or aralkyl group, or a biotin group of the formula (a) described in claim 1; $Q^-$ is a counter anion; $R^1$ is an oxygen atom, a sulfur atom or a methylene group; and m is 0 or 1.

3. A compound according to claim 1, wherein $W_1$ is a $C_1$–$C_{20}$ alkyl group.

4. A compound according to claim 1, wherein $W_1$ is a phenyl group which may be substituted with at least one $C_1$–$C_{10}$ alkyl group.

5. A compound according to claim 1, wherein $W_1$ is a nitrogen-containing heterocyclic group whose nitrogen atom may be quaternized with a hydrogen atom, a straight chain, branched chain or cyclic saturated or unsaturated aliphatic hydrocarbon group, a substituted or unsubstituted aryl or aralkyl group, or a biotin group represented by the formula (a) and whose ring may be have substituent(s).

6. A compound according to claim 5, wherein $W_1$ is selected from the group consisting of the following formulas:

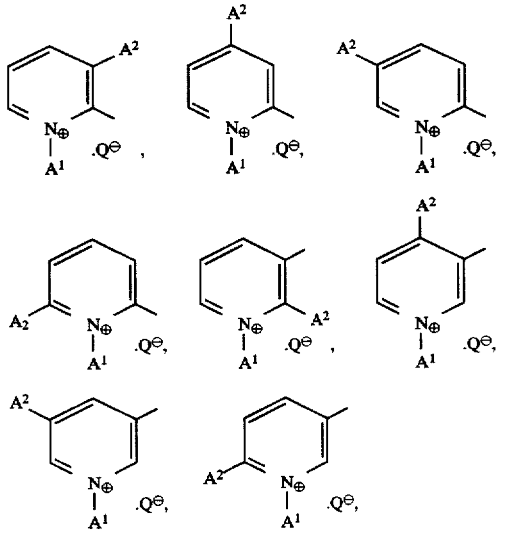

-continued

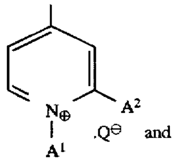

and

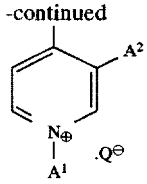

wherein $A^1$ is not present (in this case, neither + of nitrogen atom nor $Q^-$ is present), or is a hydrogen atom, a $C_1$–$C_{10}$ alkyl group, an aryl or aralkyl group which may be substituted with at least one $C_1$–$C_{10}$ alkyl group, or a biotin group of the formula (a) described in claim 1; $A^2$ is a hydrogen atom, a halogen atom, a $C_1$–$C_{10}$ alkyl group, a $C_1$–$C_{10}$ alkoxy group, or an aryl or aralkyl group which may be substituted with at least one $C_1$–$C_{10}$ alkyl group, with a hydrogen atom, a chlorine atom, a bromine atom, a methyl group or a methoxy group being preferred; and $Q^-$ is a counter anion.

7. A compound according to claim 5, wherein $W_1$ is a pyridyl or pyridinium group whose nitrogen atom may be quaternized with a $C_1$–$C_{10}$ alkyl group (e.g. a methyl group) or a biotin group of the formula (a) and whose ring may be substituted with at least one $C_1$–$C_{10}$ alkyl group.

8. A compound according to claim 2, wherein $W_1$ is selected from the group consisting of the following formulas:

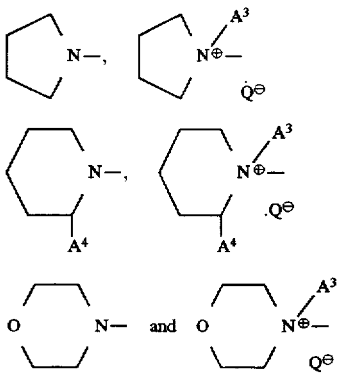

wherein $A^3$ is a hydrogen atom, a $C_1$–$C_{10}$ alkyl group, a phenyl group which may be substituted with at least one $C_1$–$C_{10}$ alkyl group, or a biotin group of the formula (a) described in claim 1; $A^4$ is a hydrogen atom or a phenyl group which may be substituted with at least one $C_1$–$C_{10}$ alkyl group, with a hydrogen atom or a methyl group being preferred; and $Q^-$ is a counter anion.

9. A compound according to claim 1, wherein $W_1$ is a pyrrolidyl, piperidyl, pyrrolidinium or piperidinium group whose 1-position is substituted with a $C_1$–$C_{10}$ alkyl group or a substituted or unsubstituted aryl or aralkyl group, or a pyrrolidinium or piperidinium group whose nitrogen atom is quaternized with a $C_1$–$C_{10}$ alkyl group, a substituted or unsubstituted aryl or aralkyl group, or a biotin group of the formula (a) described in claim 1.

10. A compound according to claim 9, wherein $W_1$ is selected from the group consisting of the following formulas:

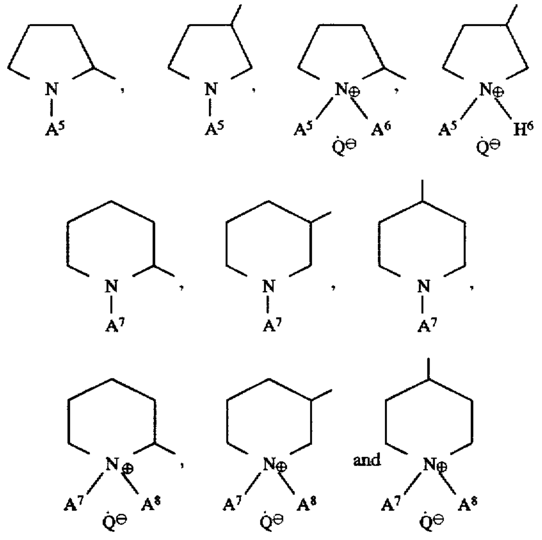

wherein $A^5$ and $A^7$ are each independently a $C_1$–$C_{10}$ alkyl group, or a phenyl or benzyl group which may be substituted with at least one $C_1$–$C_{10}$ alkyl group; $A^6$ and $A^8$ are each independently a hydrogen atom, a $C_1$–$C_{10}$ alkyl group, a phenyl or benzyl group which may be substituted with at least one $C_1$–$C_{10}$ alkyl group, or a biotin group of the formula (a); and $Q^-$ is a counter anion.

11. A compound according to claim 1, wherein —$W_2$—Z is a nitrogen-containing heterocyclic group whose nitrogen atom is quaternized with a biotin group of the formula (a) described in claim 1 and whose ring may have substituent(s).

12. A compound according to claim 11, wherein —$W_2$—Z is a pyridinium group whose nitrogen atom is quaternized with a biotin group of the formula (a) described in claim 1 and whose ring may be substituted with at least one $C_1$–$C_{10}$ alkyl group or at least one substituted or unsubstituted aryl or aralkyl group.

13. A compound according to claim 11, wherein —$W_2$—Z is a pyridinium group whose nitrogen atom is quaternized with a biotin group of the formula (a) and whose ring may be substituted with at least one $C_1$–$C_{10}$ alkyl group.

14. A compound according to claim 11, wherein —$W_2$—Z is selected from the group consisting of the following formulas:

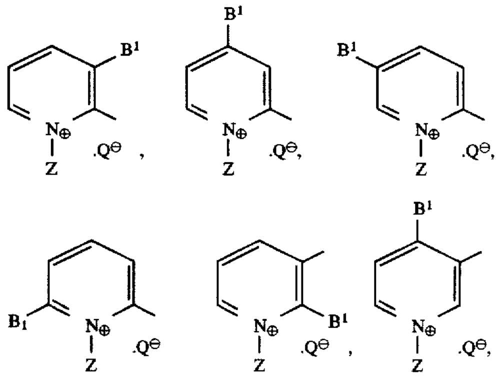

-continued

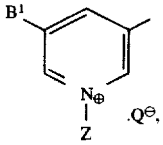

,

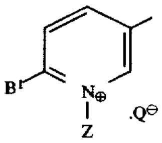

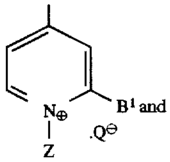

and

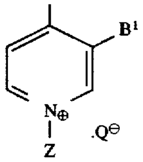

wherein $B^1$ is a hydrogen atom, a halogen atom, a $C_1$–$C_{10}$ alkyl group, a $C_1$–$C_{10}$ alkoxy group,, or an aryl or aralkyl group which may be substituted with at least one $C_1$–$C_{10}$ alkyl group, with a hydrogen atom, a chlorine atom, a bromine atom, a methyl group or a methoxy group being preferred; Z is as defined in claim 1; and $Q^-$ is a counter anion.

15. A compound according to claim 1, wherein —$W_2$—Z is a quaternary ammonium group represented by the following formula (f):

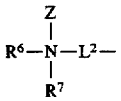

(f)

wherein $R^6$ and $R^7$ are each independently a straight chain, branched chain or cyclic saturated or unsaturated $C_1$–$C_{10}$ aliphatic hydrocarbon group or a substituted or unsubstituted aryl or aralkyl group; Z is a biotin group of the formula (a) described in claim 1; and $L^2$ is a single bond or an o-, m- or p-phenylene group which may be substituted with a $C_1$–$C_{10}$ alkyl group.

16. A compound according to claim 1, wherein —$W_2$—Z is a pyrrolidinium or piperidinium group whose nitrogen atom is quaternized with a biotin group of the formula (a) described in claim 1, a $C_1$–$C_{10}$ alkyl group or a substituted or unsubstituted aryl or aralkyl group.

17. A compound according to claim 16, wherein —$W_2$—Z is selected from the group consisting of the following formulas:

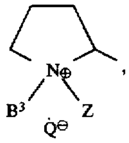

,

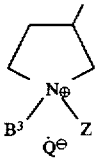

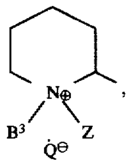

,

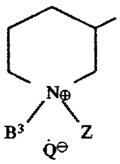

and

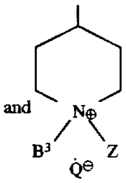

wherein $B^3$ is a $C_1$–$C_{10}$ alkyl group or a phenyl or benzyl group which may be substituted with at least one $C_1$–$C_{10}$ alkyl group, with a methyl group, an ethyl group, a phenyl group or a benzyl group being preferred; Z is as defined in claim 1; and $Q^-$ is a counter anion.

18. A compound according to claim 1, wherein X and Y are each independently an alkylene group whose main chain has 1–4 carbon atoms and which may have a methyl group as a branch.

* * * * *